(12) United States Patent
Kukharev

(10) Patent No.: US 11,487,030 B2
(45) Date of Patent: Nov. 1, 2022

(54) METHODS AND SYSTEMS FOR EARTHQUAKE DETECTION AND PREDICTION

(71) Applicant: Vadim Kukharev, Moscow (RU)

(72) Inventor: Vadim Kukharev, Moscow (RU)

( * ) Notice: Subject to any disclaimer, the term of this patent is extended or adjusted under 35 U.S.C. 154(b) by 380 days.

(21) Appl. No.: 16/876,921

(22) Filed: May 18, 2020

(65) Prior Publication Data

US 2021/0318455 A1    Oct. 14, 2021

Related U.S. Application Data

(60) Provisional application No. 63/008,575, filed on Apr. 10, 2020.

(51) Int. Cl.
| | | |
|---|---|---|
| *G01V 1/00* | (2006.01) | |
| *G01V 1/18* | (2006.01) | |
| *G01W 1/02* | (2006.01) | |
| *G01N 33/00* | (2006.01) | |

(52) U.S. Cl.
CPC ......... *G01V 1/008* (2013.01); *G01N 33/0036* (2013.01); *G01V 1/18* (2013.01); *G01W 1/02* (2013.01); *G01V 2210/74* (2013.01)

(58) Field of Classification Search
None
See application file for complete search history.

(56) References Cited

U.S. PATENT DOCUMENTS

| | | | | |
|---|---|---|---|---|
| 5,625,138 A | * | 4/1997 | Elkins | G01V 1/008 436/25 |
| 7,277,797 B1 | * | 10/2007 | Kunitsyn | G01V 1/008 702/15 |
| 2008/0183393 A1 | * | 7/2008 | Rundle | G01V 1/008 702/15 |
| 2008/0234940 A1 | * | 9/2008 | Mizrahi | G01V 1/008 702/15 |
| 2009/0033511 A1 | * | 2/2009 | Komiya | G08B 21/10 340/690 |
| 2011/0270793 A1 | * | 11/2011 | Bertogg | G06Q 40/06 706/50 |
| 2018/0376314 A1 | * | 12/2018 | Allen | G01V 1/008 |
| 2020/0225373 A1 | * | 7/2020 | Ouzounov | G01V 1/008 |

FOREIGN PATENT DOCUMENTS

CN            105891877 A  *  8/2016

* cited by examiner

*Primary Examiner* — Lina M Cordero
(74) *Attorney, Agent, or Firm* — Nadya Reingand

(57) ABSTRACT

Disclosed are methods and systems for detecting and predicting events of increased seismic activity (i.e. earthquake activity). The methods include providing data catalogs, constructing magnitude versus time coordinate graphs, identifying energy levels of the graphs, and identifying further the obliquity angles of maximum and minimum energy levels and average increments between minimum and maximum energy levels. The methods also comprise constructing time arrows using the identified information, identifying energy centers via the time arrows, and analyzing variability throughout the seismic structure to predict a future event. Also disclosed are methods for predicting events based on attenuation wedge and energy parallelogram analysis.

16 Claims, 48 Drawing Sheets

A retroforecast of the Haiti earthquake of January 12, 2010
(earthquake preparation took 2.5 - 5 years)

( W - thrmodynamic probability ( statistic weight))

METHODS AND SYSTEMS FOR EARTHQUAKE DETECTION AND PREDICTION

CROSS-REFERENCE TO RELATED APPLICATIONS

The present patent application claims priority to U.S. Provisional Patent Application Ser. No. 63/008,575, filed Apr. 10, 2020, said application and its disclosures being incorporated herein by reference in their entireties.

FIELD OF THE INVENTION

This invention relates to the field of measurement, detection, and prediction of seismic activity using nonlinear thermodynamics.

BACKGROUND ART

There has long been a need for identifying distinctive signs of a coming earthquake based on analysis of the energy process structure (i.e. the magnitude in terms of energy, dependent on time) from the perspective of nonlinear thermodynamics.

Numerous failures forecasting particular seismic events have led to pessimistic thoughts about the possibility of reliable short-period forecasting (i.e. days, hours) of strong seismic events (i.e. events with a magnitude of 6 or greater), let alone relatively weak events (i.e. those with a magnitude of 3-5). Also, the seismic process in focal point areas is normally typified as stochastic, whereas the main researching effort is aimed at identifying statistically-significant patterns (e.g., discovering temporal and spatial periodicity of strong earthquakes). The statistical approach is, in principle, incapable of securing short-term event forecasting.

On the whole, the energy structure of seismic processes in focal point areas, is not normally analyzed, as there is an a priori belief that seismic processes are stochastic by nature, having no deterministic elements. The present invention describes a solution to forecasting seismic processes.

SUMMARY OF THE INVENTION

The present invention describes methods for predicting seismic events comprising (1) providing one or more data catalogs for an area, (2) constructing magnitude-time coordinates for one or more information cells within said area, said magnitude-time coordinates forming a seismic process structure, (3) identifying energy levels of the seismic process structure, (4) identifying elements within the seismic process structure, the identified elements comprising: obliquity angles of maximum energy levels, obliquity angles of minimum energy levels, and a potential of the seismic process structure, the potential comprising an average increment between minimum and maximum energy levels of the seismic process structure, (5) constructing one or more time arrows and calculating one or more measuring angles of the one or more time arrows, the one or more measuring angles of the one or more time arrows being relative to a time axis of the seismic process structure, (6) identifying instant energy centers, the instant energy centers comprising variations in energy levels, (7) analyzing a variability of: the elements within the seismic process structure, the one or more time arrows and the one or more measuring angles, and the instant energy centers, and (8) predicting a seismic event based on said analyzing.

In some aspects, the instant energy centers are indicated by an attenuation wedge, the attenuation wedge being locatable along a graphical seismic process representation.

In some aspects, the attenuation wedge is modeled using an attenuation oscillations equation, the attenuation oscillations equation being $X1(t)=A \cos \omega t \cdot \exp(-\Delta t)$.

In some aspects, characteristics of the attenuation wedge are analyzed separately for positive components and negative components of the series, $X1(t)$.

In some aspects, the method further comprises calculating one or more points of intersection between upper and lower regression curves formed as results of the separate analyzing of the positive components and the negative components of the series, $X1(t)$.

In some aspects, the method further comprises detecting heat anomalies prior to the seismic event.

In some aspects, the method further comprises building one or more energy parallelograms.

In some aspects, the method further comprises detecting radon anomalies prior to the seismic event.

In some aspects, the method further comprises constructing an energy curve, $A^2(\omega)$, the curve having the following parameters: $\omega_0$, $\alpha$, $\lambda$, and F, identifying a point in time when a system depicted by the energy curve resembles a wedge, computing a change in the energy curve based on an amplitude of a counter-entropy event, and approximating a number of iterations until a significant seismic event is determined to occur, the number of iterations being translatable into a time value, wherein the time value is used to predict an onset of the seismic activity.

In some aspects, the method further comprises detecting an ultra-small event.

In some aspects, the method further comprises analyzing a focal point's energy structure.

In some aspects, the method further comprises detecting atmospheric pressure changes.

In some aspects, a forecast is provided 1-3 months in advance of the seismic event.

In some aspects, a forecast is provided 1-10 days in advance of the seismic event.

In some aspects, the method further comprises receiving data from local seismometers.

In some aspects, the method further comprises performing a geodynamic monitoring with inertial seismometers.

BRIEF DESCRIPTION OF THE DRAWINGS

The present invention will now be discussed in further detail below with reference to the accompanying figures, briefly described as follows:

FIG. 47A—basic time series. FIG. 47B—series of first differences. FIG. 47C—positive and negative component series of first differences, the dotted one—series of local maximums (and minimums). FIG. 47D—calculation of regression equation parameters.

DETAILED DESCRIPTION OF THE PREFERRED EMBODIMENTS

Figure 1:
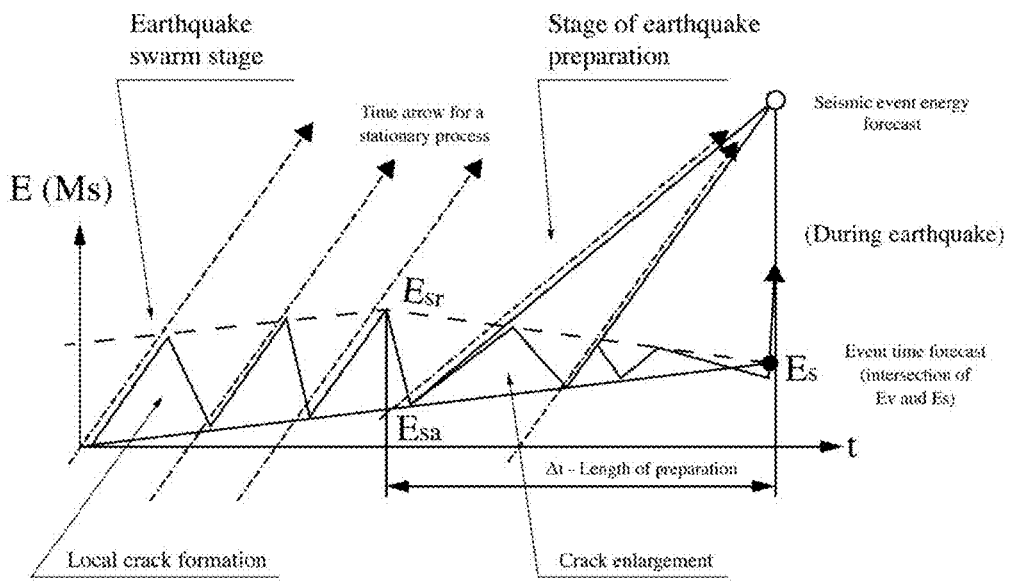
FIG. 1. A model of the energy process illustrating the preparation stages of a seismic event.
Figure 2:
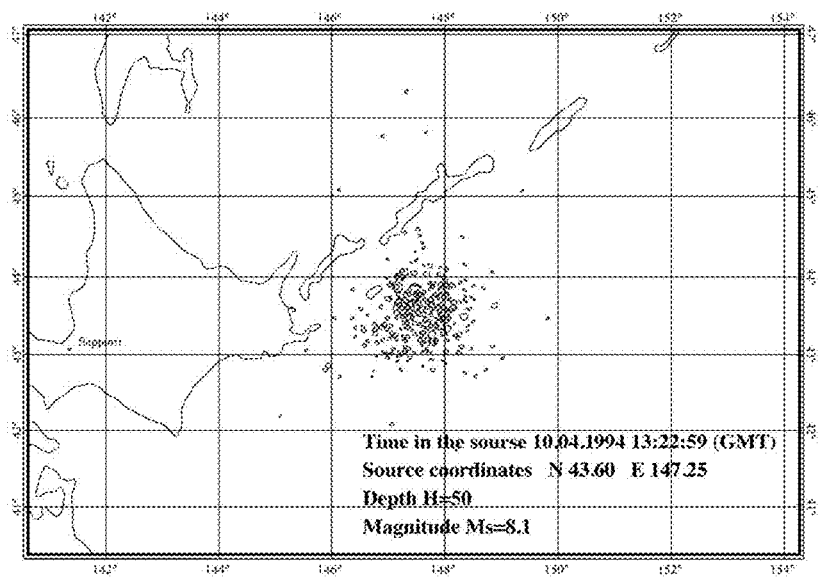
FIG. 2. The location of the Shikotan earthquake in 1994.

In the following description, for purposes of explanation, specific examples are set forth to provide a thorough understanding of the present invention. However, it will be apparent to one skilled in the art that these specific details are not required in order to practice the present invention. The same techniques can easily be applied to other types similar systems.

It is known in the art that:

$$M = k \log \frac{A_i}{A_0},$$

where $A_0$ is a signal registered by a reference instrument at a distance of 100 km from a typical earthquake; and $A_i$ is a signal from a current seismic event.

A seismic focal point is a certain geological area, within which accumulation and discharge of various types of energy (elastic, thermal and others) take place under the impact of different external forces (e.g., compression, stretching, twisting, shifting along the fault).

From the point of view of practical seismology, the most interesting kind of energy is the elastic seismic energy generated during earthquakes (not more than 5-10% of the whole amount within the focal point). The magnitude (although there are many experimental mathematical descriptions) is an integral energy characteristic of a seismic focal point. One commonality between seismic focal points is an anomalous accumulation of energy under the impact of external forces of a different nature. Some artisans have expressed an opinion that of all the existing physical models describing natural phenomena, thermodynamics (particularly, its second law) allows, in principle, predicting a future event. At the beginning of the 20th century, quantitative evaluation of entropy was introduced within thermodynamics—a parameter whose value is proportionate to the logarithm of the system status probabilities, i.e. $S = k \log_2 W$ Another interpretation of the entropy concept, applicable to continuous geological media is that entropy may be defined as a logarithm of the relation between the system's phase space volumes, parts of which are in significantly different energy states, i.e.:

$$S = k \log_2 \frac{V_i}{V_0}$$

With such a physical interpretation, the mathematical description of the entropy, S, according to Boltzmann-Penrose and the magnitude, $M_r$, according to Richter, agree within an invariable. In the physical sense, magnitude is analogous to informational entropy, and given the equivalence of the mathematical formalization, the time dependence of magnitude for a focal point area characterizes entropy changes in this area of the geological space.

It follows from the second law of thermodynamics that entropy steadily goes up in closed irreversible systems. At the same time, according to the first law of thermodynamics, energy balance (conservation) must be maintained within the system. It is known that evolutionary stages of non-isolated complex systems can be marked with an overall entropy decrease of $$\frac{ds}{dt} < 0.$$

More so, for systems that exchange energy or substances with the external environment, the entropy change is perceived as a sum.

One of the components is conditioned by the exchanges under way, or $d_e s$ (also termed entropy flow). The other component is dependent on the processes within the system, or $d_i s$ (also termed production of the entropy). Therefore, $$\frac{ds}{dt} < \frac{d_1 s}{dt} + \frac{d_e s}{dt}$$

In such systems, entropy decay takes place in correspondence with the system energy levels. As for seismic focal points, energy and entropy levels correspond to the modular-hierarchical organization of the geological medium.

A seismic focal point is not an absolutely closed system, yet when pumping in external energy, a focal point space (phase volume) during preparation for seismic events can be regarded as a temporarily closed system, in which entropy is growing due to disruption under the impact of external forces of the space primary structure. As the old geological space structure is disintegrating, a new structure is taking shape, which leads to entropy decrease rather than any increase. During an earthquake, the system opens, spasmodically producing energy, while the entropy, likewise spasmodically, decreases, until the cycle begins to occur again.

Based on the above, temporal development of energy processes in seismic focal points was analyzed. The principal model of an energy process at the stage of a seismic event's preparation is presented in FIG. 1. Regardless of the object scale (a specimen of 1-10 cm, a rock slab of 1-1000 m, the geological space volume of 1-100 km, etc.) crack formation occurs in the geological medium as external forces increase according to the following pattern: (1) at first, many minor cracks appear (i.e., destruction of the primary energy structure takes place), (2) then, as the external forces grow, in some parts of the geological space, crack enlargement occurs. Thus, a new energy structure is being formed in a certain part of the phase space.

Figure 3:
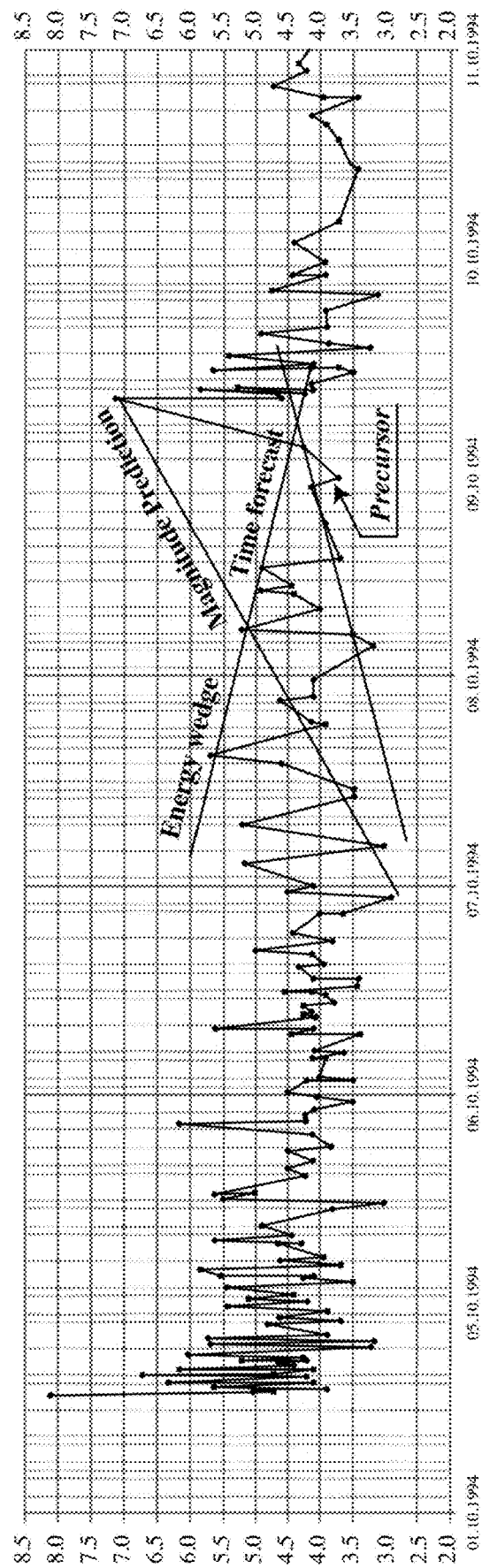
FIG. 3. An exemplary "energy wedge" formed during the aftershock of the Shikotan earthquake (a forecast scheme).
Figure 4:
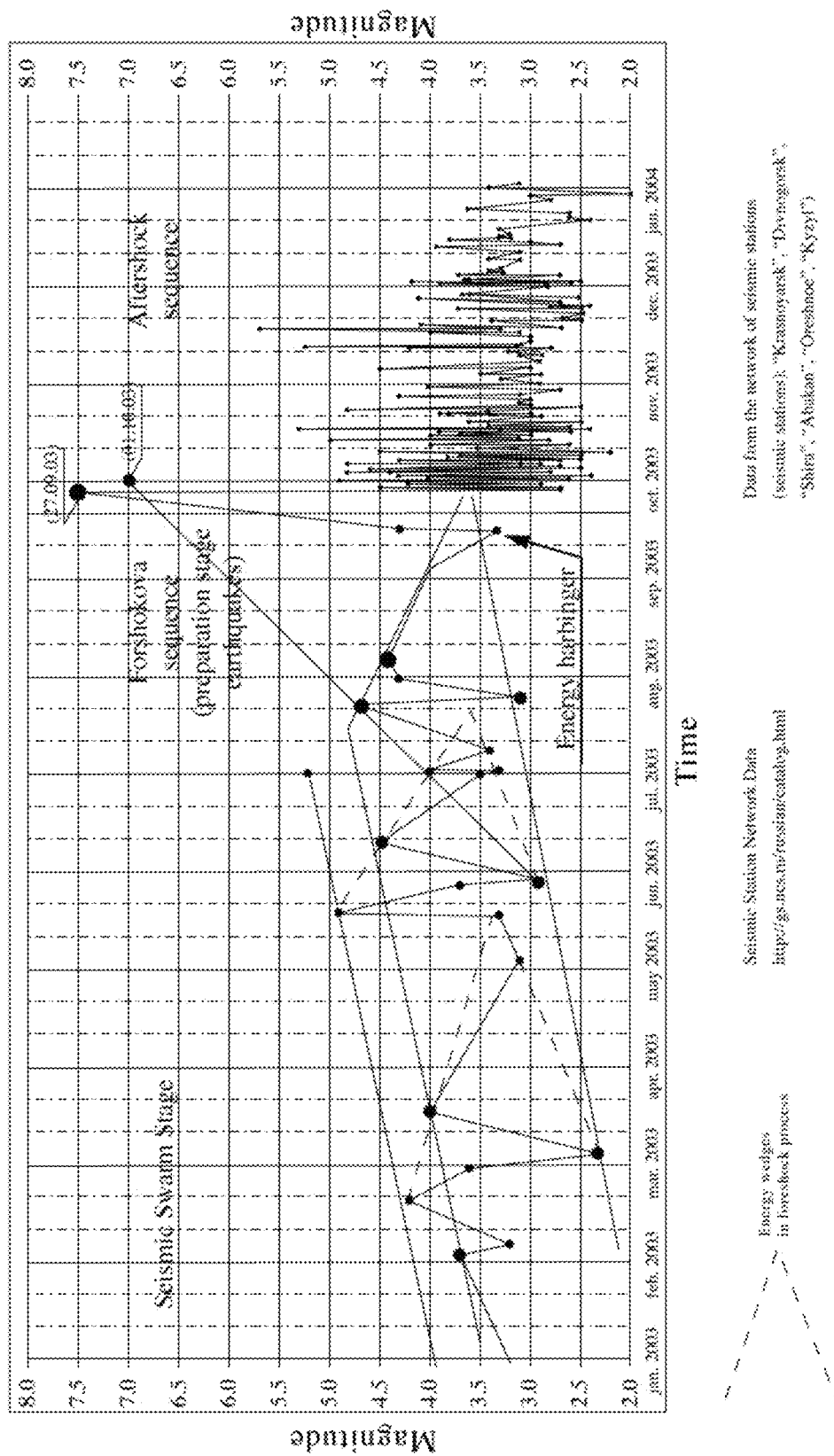
FIG. 4. A retroforecast of the Altai earthquake, from Sep. 27, 2003, according to the present invention.
Figure 5:
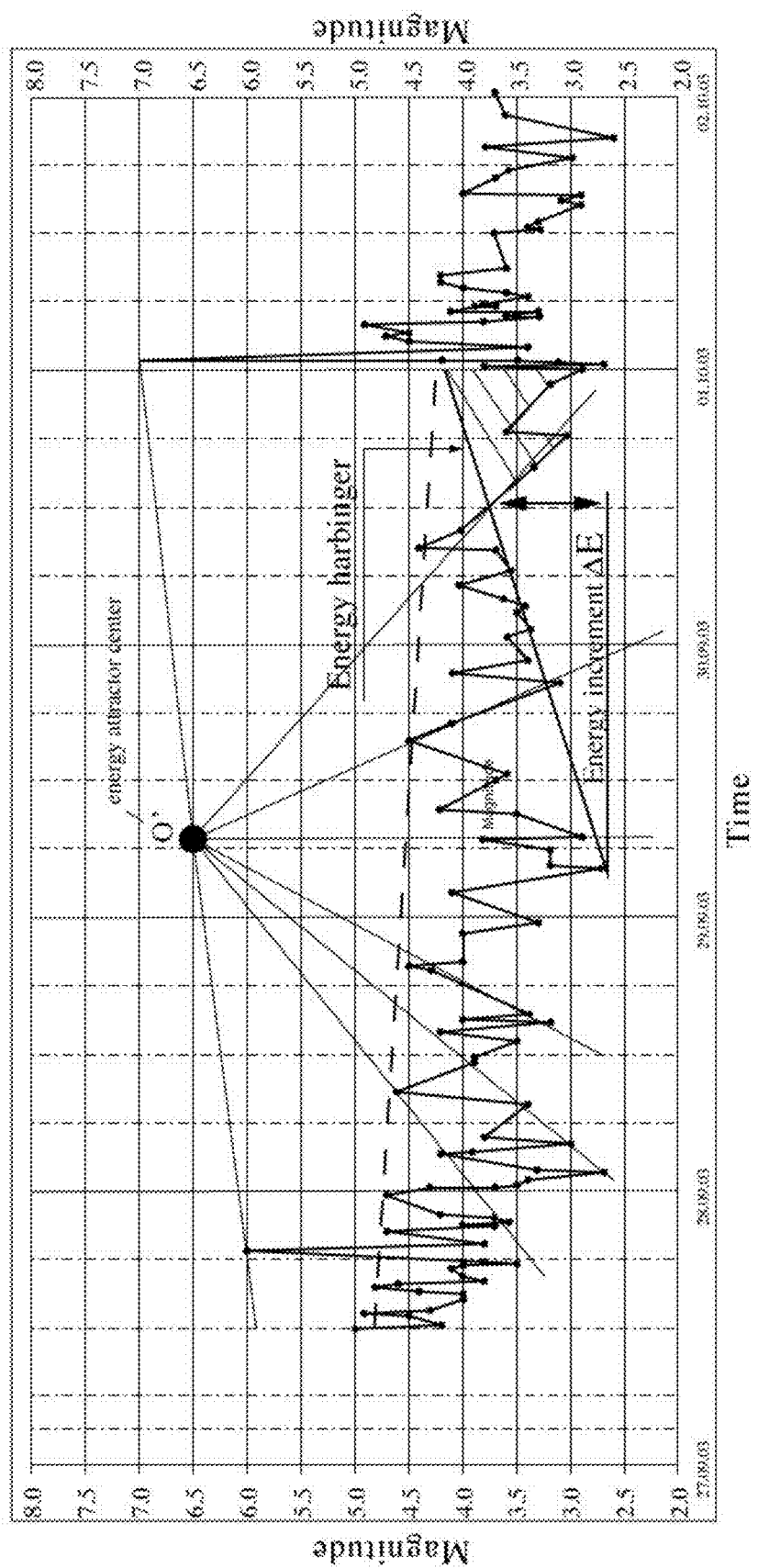
FIG. 5. A forecast of the aftershock of the Altai earthquake, from Oct. 1, 2003, according to the present invention.
Figure 6:
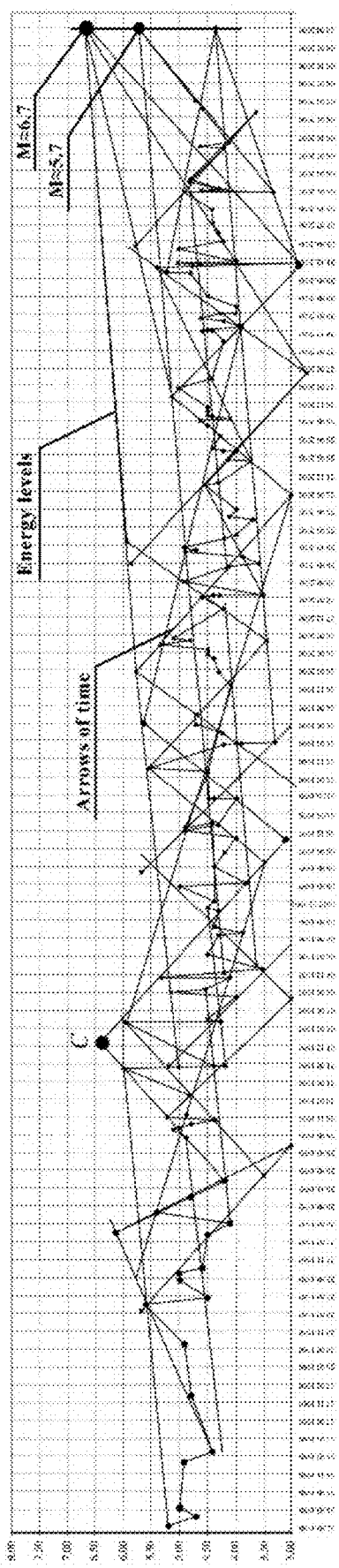
FIG. 6. An example of temporal series treatment, $M=f(t)$, near the Kamchatka peninsula.

In accordance with the second law of thermodynamics, this leads to entropy decrease and, as a result, an "energy wedge" emerges and is highly indicative of a major seismic event approaching imminently. This energy wedge is one of the main prognostic signs of a large seismic event. It also corresponds to the well-known stage of the "seismic calm," as previously noted, at which the energy level of seismic events in the area under observation decreases. According to the concentration criterion, it is at this process development stage that under the external impact, crack enlargement occurs and the plane of the future fracture is formed. The energy wedge stage corresponds to the extraction time interval in the phase space of the focal point area of a certain subarea, converging to the plane of the future fracture. Note that the external impact entropy (phase volume entropy) and the internal entropy (entropy of a phase volume part eventually directed to the plane) intersect at a level corresponding to a point in time when the energy of the rock is resisting power, and during the focal point. FIG. 3 shows an exemplary "energy wedge" being formed prior to an earthquake (forecast scheme). Examples of constructing energy wedge formations are also shown in FIGS. 4-6, 16, 17, 43, 44, and 49-54.

Such energy wedges were detected in retrospect for nearly all major earthquakes. At the forecast stage, detection of energy wedges ensures a reliable forecast of a coming earthquake in 70-75 percent of cases. During an earthquake, the system spasmodically generates energy, cumulative entropy of the focal point area spasmodically decreases with a subsequent cyclic development at the aftershock stage. Thus, the presence of an energy wedge in an entropy model explains well-known empirical facts, in particular, the seismic calm. It is not at variance with common seismological models of seismic focal points (e.g., dilatancy model, avalanche-unstable crack formation).

During preparation for seismic events, energy wedges with a magnitude of up to 4.0-5.0 are rarely registered by existing (insufficiently dense) seismic networks. It is also possible that with a magnitude of under 5.0, no clear plane fracture is formed within the focal point. Energy wedges invariably take easily registered shapes during preparation for major seismic events with magnitudes of 6.0 and greater. The present invention thus also addresses the clear necessity to monitor low-energy events in focal point areas by way of increasing the density in the observation network around a potential focal point.

Research into the structure of focal point areas in many locations confirms the adequacy of the nature of seismic processes to the model of deterministic chaos. To single out the deterministic component of the process, there are approaches developed in nonlinear thermodynamics of irreversible processes.

It is critical to note that the success of forecasting as described herein is determined not only by discovered patterns in the structure of energy processes, but also by the reliability of the input data. Specifically, (1) an energy process must contain magnitudes of the same nature and there must be no considerable time irregularities; and (2) magnitude values in the process under analysis must be of equal accuracy and must not contain systemic distortions.

In compliance with the known phenomena of the self-organization of seismic processes, the area of forecasting the future event location should be 2-10 times larger than the size of the focal point of a specific seismic event. Optimization of the forecast area size is achieved by consistent scanning of the epicentral field before receiving the stable energy temporal series relating to the chosen location.

Table 1 shows correspondence between information cells and expected magnitude events.

TABLE 1

| | |
|---|---|
| M ≈ 5.0 | R ≈ 100 km |
| M ≈ 6.0 | R ≈ 200 km |
| M ≈ 7.0 | R ≈ 300 km |
| M ≈ 8.0 | R ≈ 400 km |
| M ≈ 9.0 | R ≈ 500 km |

The Analytical Methodology of the Present Invention

Figure 55:
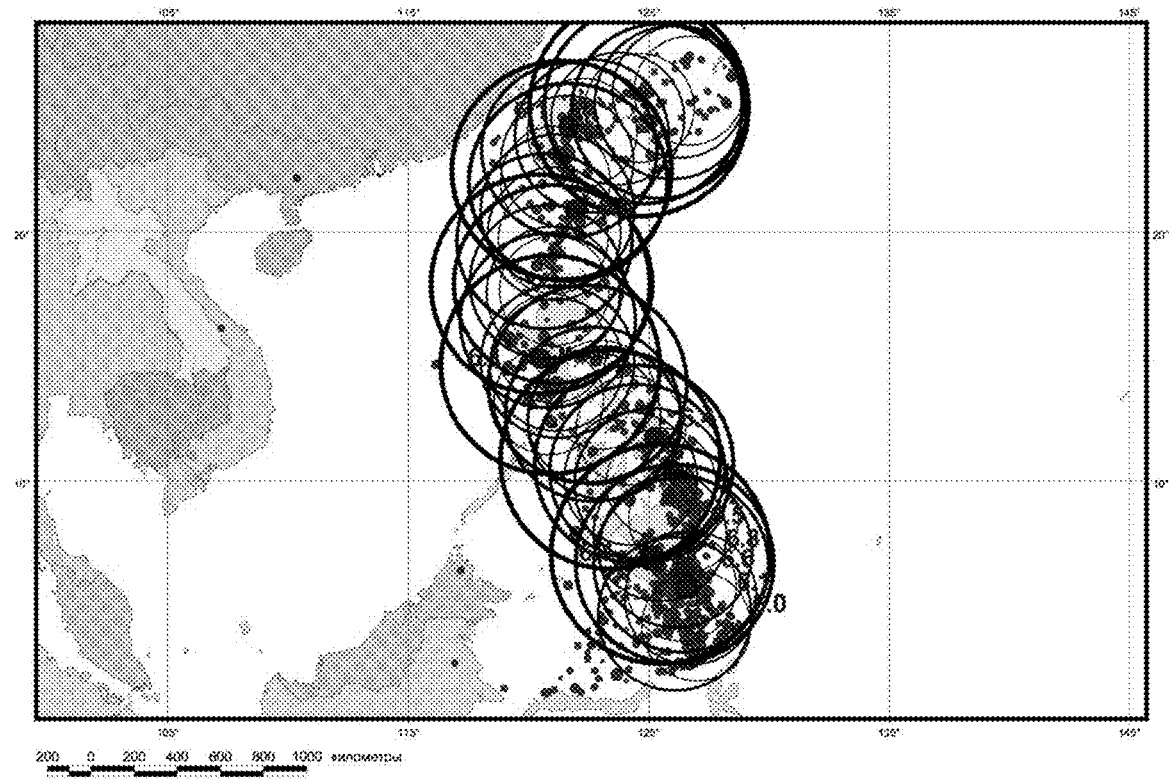
FIG. 55. Scanning the prognostic area (earthquake catalogue) with a circle or ellipse having a radius, the radius corresponding to the expected magnitude of events.

A specific sequence of steps is disclosed, the steps being combined to predict the occurrence of seismic events:
(1) Scanning the prognostic area (earthquake catalogue) with an information cell (see, e.g., FIG. 54)—i.e., a circle or ellipse having a radius, the radius corresponding to the expected magnitude of events (FIG. 55). See Table 1, which shows examples of expected magnitudes of events in terms of an expected radius based on a known magnitude, or vice versa);
(2) Constructing seismic processes in "magnitude vs. time" coordinates for each information cell;
(3) Identifying energy levels (maximums/minimums);
(4) Identifying distinctive elements of the seismic process structure, including but not limited to:
 (a) the obliquity angles of maximum, minimum, and other energy levels—α; and
 (b) assessment of the seismic process "potential" A as an average increment between minimum and maximum energy levels;
(5) Constructing time arrows and measuring angles, $\gamma_i$, i.e. obliquity angles of time arrows with respect to the "time" axis in the magnitude—time system;
(6) Identifying instant energy centers, C, which control the seismic process, the seismic process being formed due to breaks of energy levels;
(7) Analyzing the variability of the aforementioned parameters (α, Δ, C, γ) within the chosen area. An example of the process is presented in, e.g., FIGS. 3-6.

As for location of the future epicenter, the well-known forerunner technologies (e.g., seismic, electromagnetic, hydrodynamic, geochemical, biochemical) can be used rather efficiently in combination with the present invention, for specifying the location of pending major seismic events.

A Mathematical Model of the Invention, Based on a Nonlinear Oscillator

Figure 10:
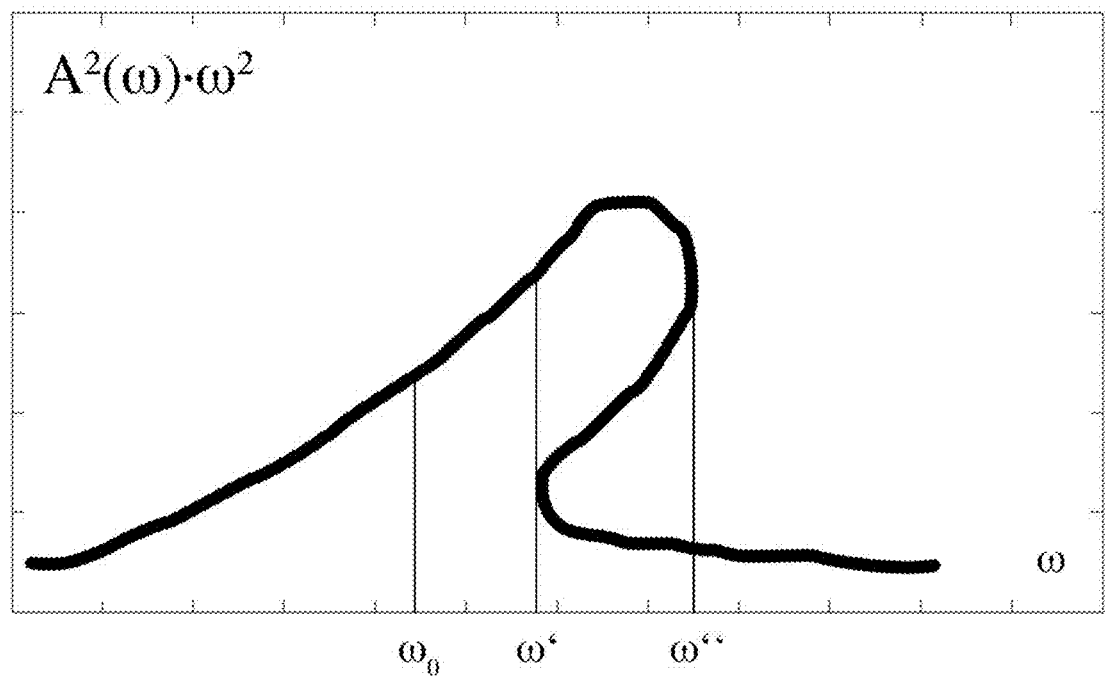
FIG. 10. A graphical example of seismic event where the external impact is strong.
Figure 11:
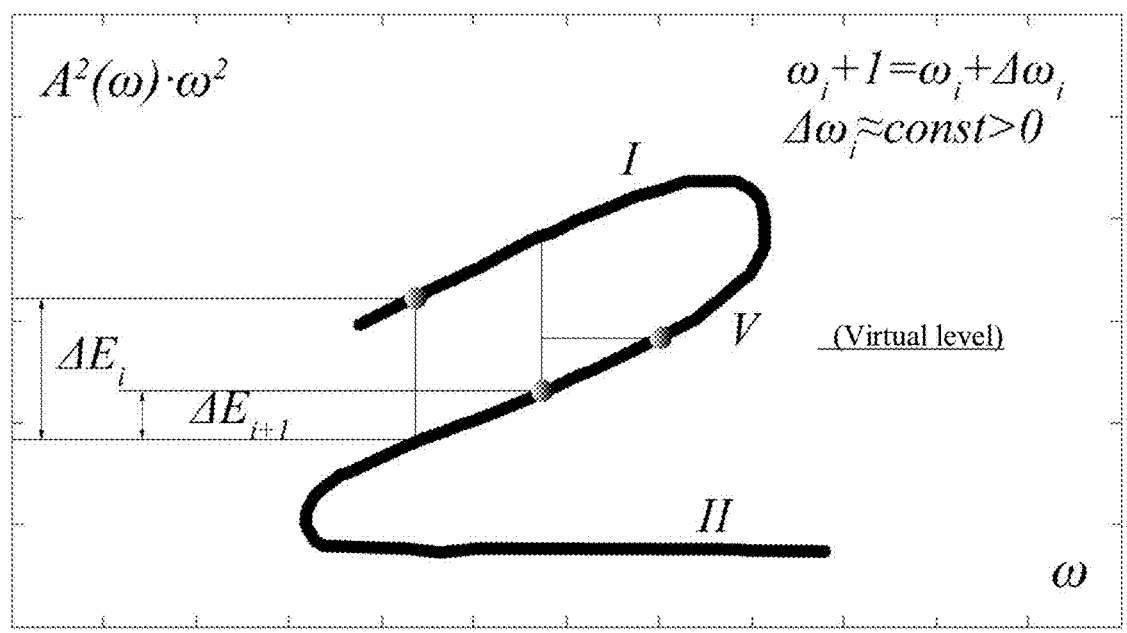
FIG. 11. A graphical depiction of the two-stage character of event development.

Specific features of the seismic process energy structure in focal point areas can be described using a mathematical model of a nonlinear oscillator, as shown in FIGS. 10-11.

To describe seismic events of interest, the following approach is suggested based on the equation for pumping external energy into a nonlinear pendulum:

$$x'' - \alpha \cdot x' + \omega_0^2 x^\lambda = F \cdot \sin(\omega \cdot t),$$

where $$x'' = \frac{d^2 x}{dt^2}, \quad x' = \frac{dx}{dt},$$

'α' is the attenuation parameter, '$\omega_0$' is the nonlinear pendulum's own frequency, 'λ' is the parameter of nonlinearity, "F" represents coercive forces, and 't' represents time. The following is also given:

$$x = A(\omega) \cdot \sin(\omega t + y),$$

where y is a phase.

Figure 7:
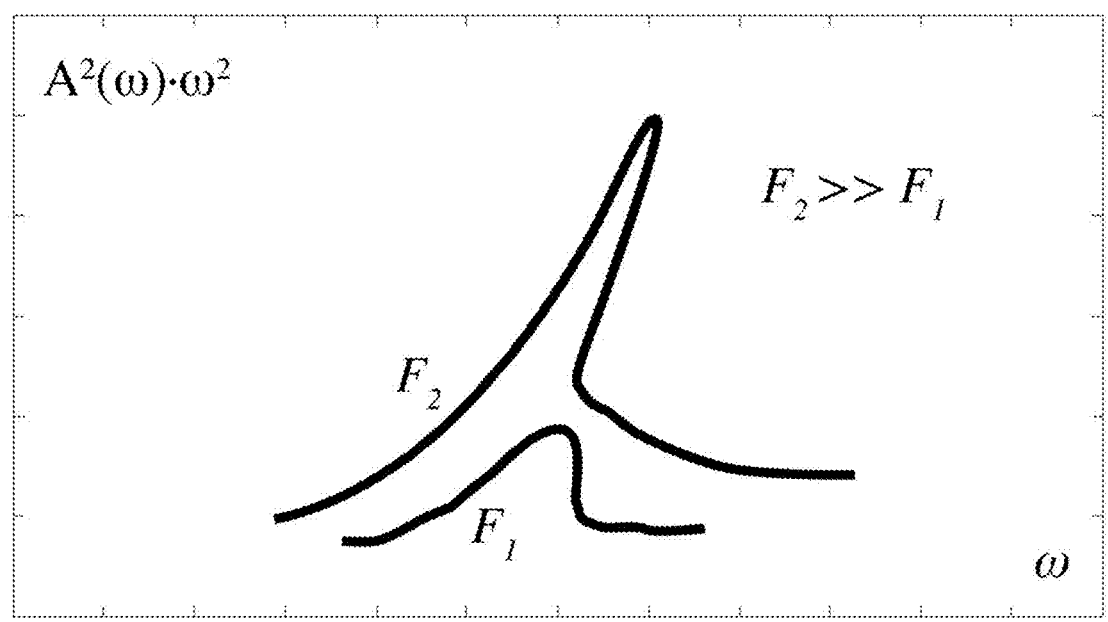
FIG. 7. A graphical example of boosting (i.e. pumping) a nonlinear pendulum.

As an example, consider an event when the external impact is weak—that is, the external impact follows the path of $F_1$, as shown in FIG. 7.

Figure 9:
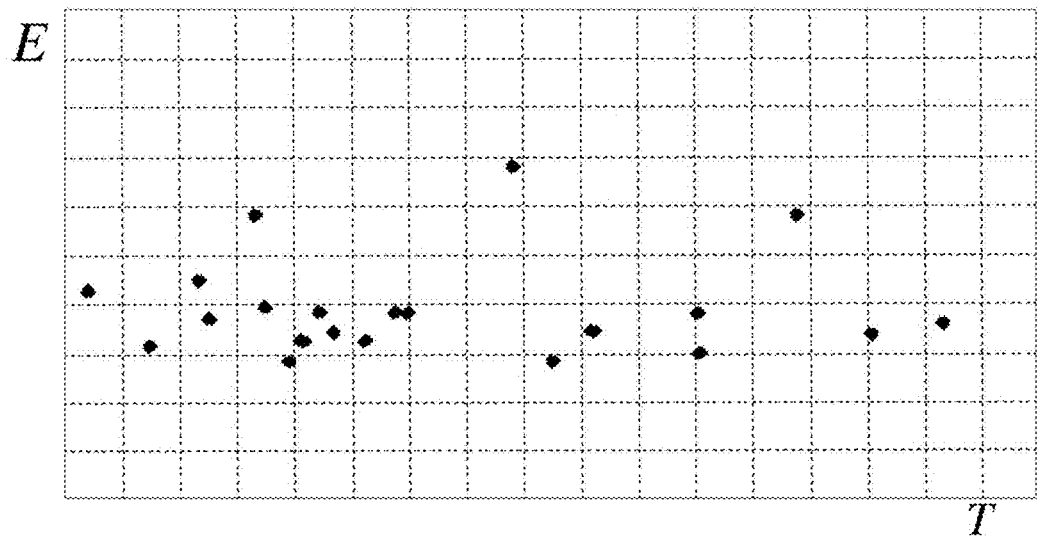
FIG. 9. A plot diagram showing the changing energy of a seismic event over time.

When the frequency of the external force is ω, the energy is pumped up to the value of $A_i^2 \cdot \omega^2$, and then followed by its subsequent decrease to zero. Since $\Delta\omega_i$ is a random value, the event energy rises or falls in a random fashion. This is often observed in reality. See FIG. 9 as an example of a change of a recorded event energy, as illustrated over time.

Figure 8:
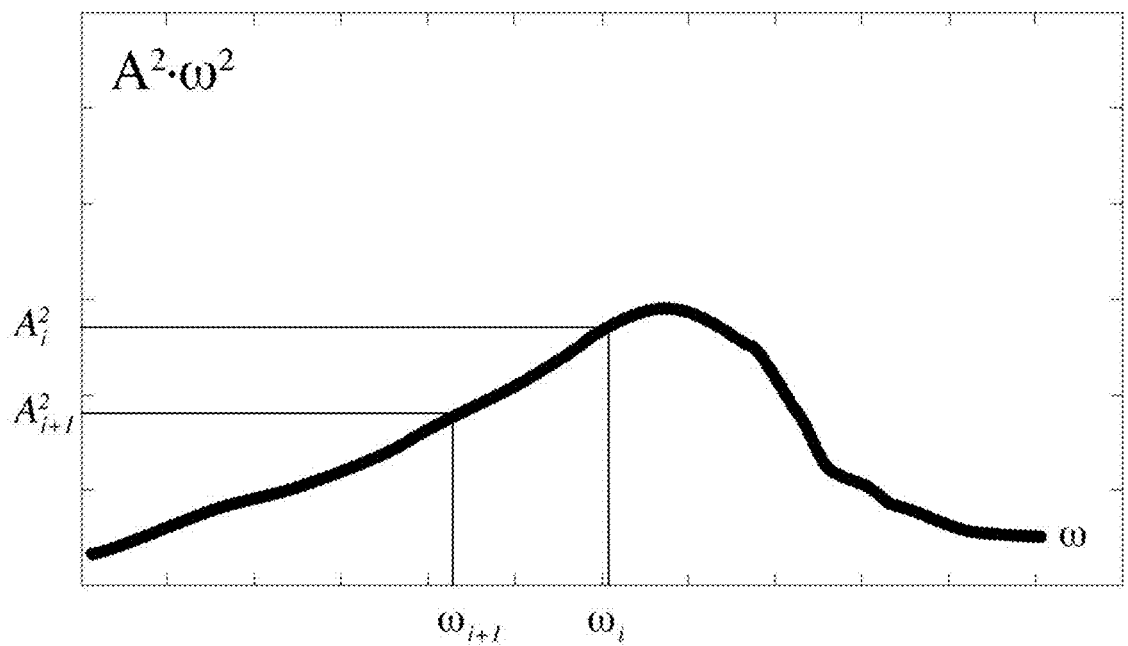
FIG. 8. A graphical example of a seismic event where the external impact is weak.

As a second example, consider an event where the impact force, following the path of $F_2$, is large. FIG. 8 shows an exemplary recording of a large seismic event. The space from 0 to ∞ at ω can be divided into three sections: (1) (0, ω'), (2) (ω', ω"), and (3) (ω", ∞). At 0<ω<ω', in the section (0, ω'), energy events will change randomly. This resembles system behavior when $F_1 \ll F_2$). If ω'<ω<ω", and when the system has entered into its appendix period. The two-stage character of the events development is revealed graphically in FIG. 11.

Figure 12:
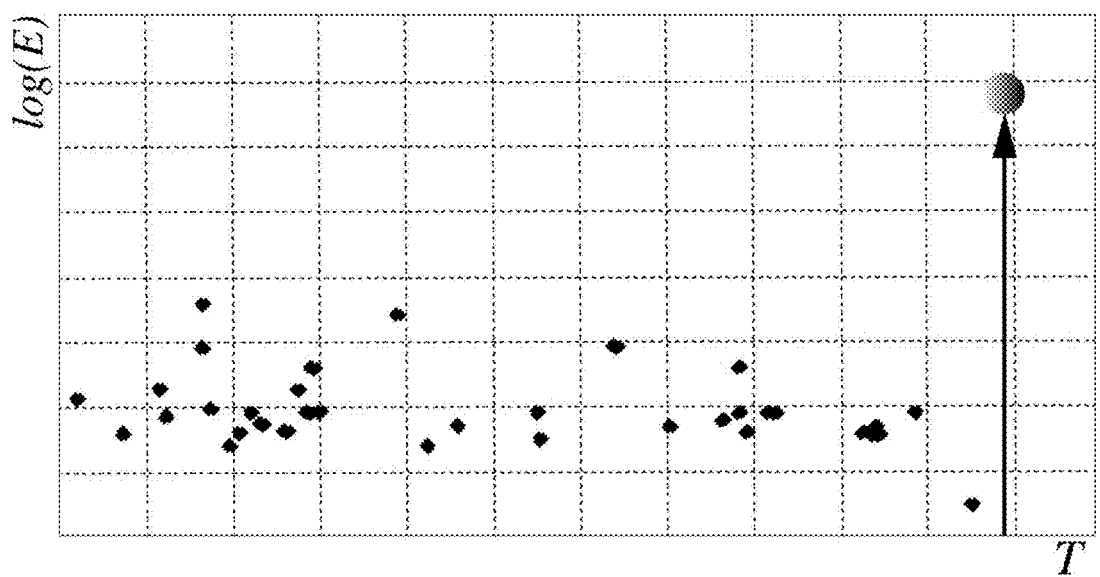
FIG. 12. The event energy is $\Delta E_{i+1}$.
Figure 13:
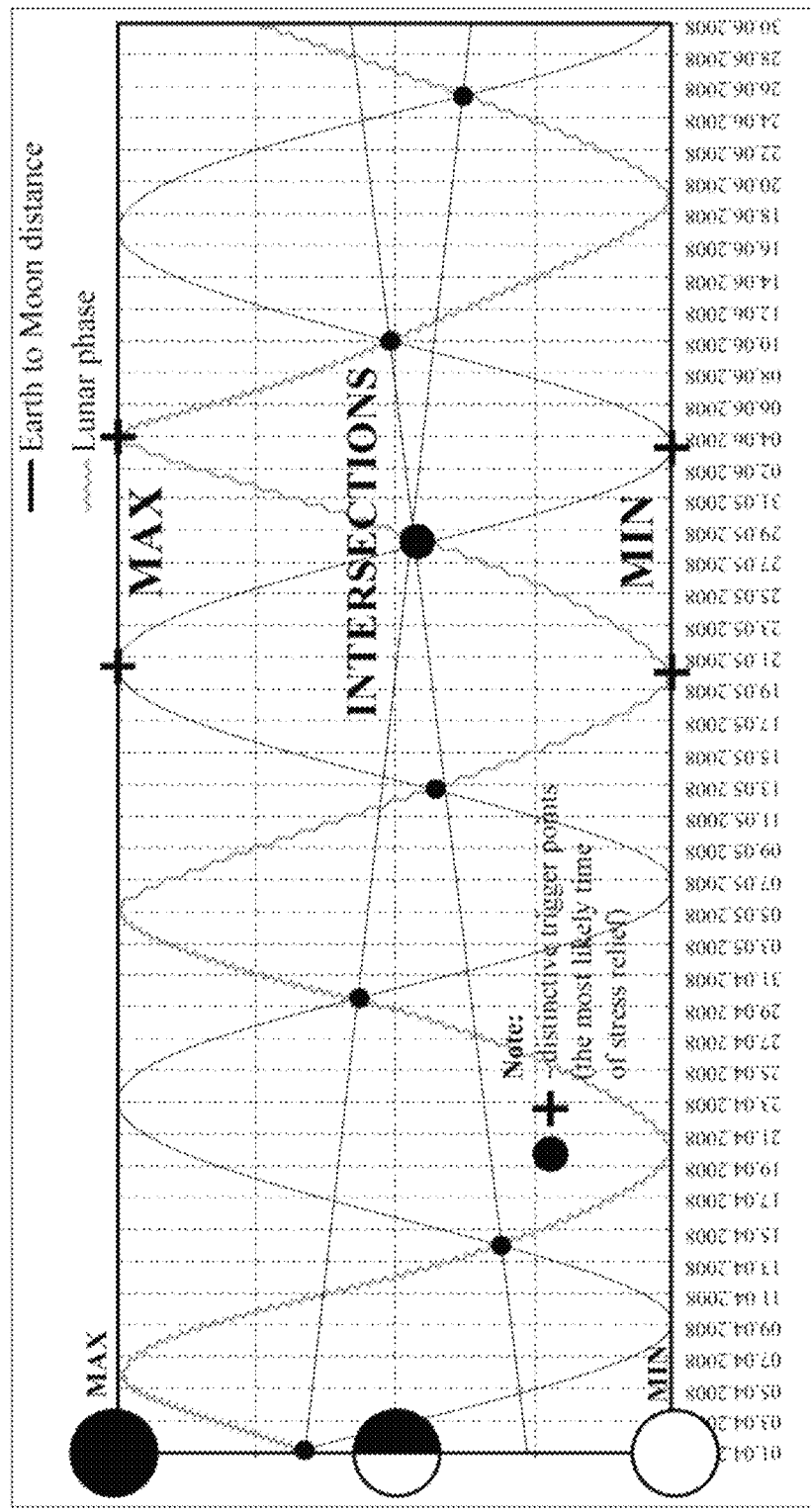
FIG. 13. A graphical depiction of distinctive changes of parameters of the Earth's orbit position relative to the Moon and the Sun.

Due to formation of minor cracks, the system falls from a stable level, I, to a virtual level, V, having an energy of $\Delta E_i$ (it is noted that the entropy in this part of the Earth's crust is increasing at this point), microcracks merge to form larger cracks or combinations of microcracks (the energy in this part of the Earth's crust changes at a rate of $\Delta\omega_i$=const>0). The event occurs with the energy of $\Delta E_{i+1}$. FIG. 12 shows an example of how events of the entropy and events of the counter-entropy nature oscillate and vary relative to one another.

In the approximation of a single nonlinear oscillator, over time, $\omega_i$ will become bigger than ω" (i.e., $\omega_i \geq \omega$") and a major event will occur with an energy larger than normal (see FIG. 1, which, as discussed, shows a simplified exemplary detected wedge, which is indicative of an imminent seismic event of relevance).

Entering the area, ω"<ω<∞, events of comparatively low energy are witnessed, and the system falls from the second stable level, II. FIG. 11 illustrates where the second stable level, II, flattens (i.e. a plateauing level occurs during level II). $\Delta\omega_i$ is a random value but is always greater than zero. As the system passes through the second stable level II curve, the system will eventually fall below the threshold line, ω', as seen in FIG. 10, and the process will start over.

Forecasting earthquakes with a single source, according to the present invention, comprises:

(1) Constructing, based on a compilation of data from 20+ years of observations, an energy curve, $A^2(\omega)$, the curve having parameters: $\omega_0$, α, λ, and F.

(2) Identifying a point in time when the system, as graphically depicted, resembles a wedge, i.e. ω'<ω<ω," and computing $\Delta\omega_i$ based on the amplitude of the counter-entropy event.

(3) Determining an approximate number of iterations, $$\frac{\omega'' - \omega'}{\Delta\omega_i},$$

until a large (i.e. significant) seismic event is predicted to occur, the number of iterations being translatable into a time value, and wherein the time value is used to predict an onset of the significant seismic event by converting the number of iterations into time and adding the time value to the present time and/or any other particular time based on the desired resulting calculation.

The definition of an ultra-small event is also of particular importance because an ultra-small seismic event very often forms at the very beginning of a detectable larger seismic event; i.e., the existence of an ultra-small event, if detectable, is a forerunner of a much larger event.

An automated technology of detecting wedges in the structure of experimental evidence (seismic catalogs) makes it possible to enhance reliability and justification of forecasts of larger seismic events. An analysis of the focal points' energy structure allows for assessing the energy potential of the focal point, i.e., the expected magnitude of a future event.

The Impact of External Factors on the Occurrence of a Seismic Event

Regarding a timed forecast, there are different factors triggering the focal point's (earthquake) actuation. In particular, the Earth's tides related to the gravitational pulls in the Earth-Moon-Sun system. Based on the analysis of world seismic catalogs [including but not limited to NEIC] and an assessment of the gravitational impacts that the Moon and Sun have on the lithosphere, a link exists, and is detectable, between strong earthquakes (M>7.0) and particular changes of the parameters of the Earth's orbit position relative to the Moon and Sun (i.e. in the Earth-Moon-Sun system). The quantitative and graph-analytic presentation of such effects is provided in Table 2.

Table 2 shows the percentage of correlations between strong earthquakes and distinctive changes of parameters of the Earth's orbit position in the Earth-Moon-Sun system, i.e., relative to the Moon and the Sun. From the Table, it is seen that events having a higher magnitude (M) have a higher percentage of correlations to the Earth's orbit position, while events having a lower magnitude have a lower percentage of correlations. For the greatest magnitude events, the correlation percentage is about double the lowest magnitude recorded in this particular study.

TABLE 2

| M | Max (%) | Intersections (%) | Min (%) | Uncertainty (%) |
|---|---------|-------------------|---------|-----------------|
| "7-9" | 12 | 51 | 27 | 10 |
| "6-7" | 20 | 41 | 29 | 10 |
| "5-6" | 37 | 25 | 17 | 21 |

Figure 14A:
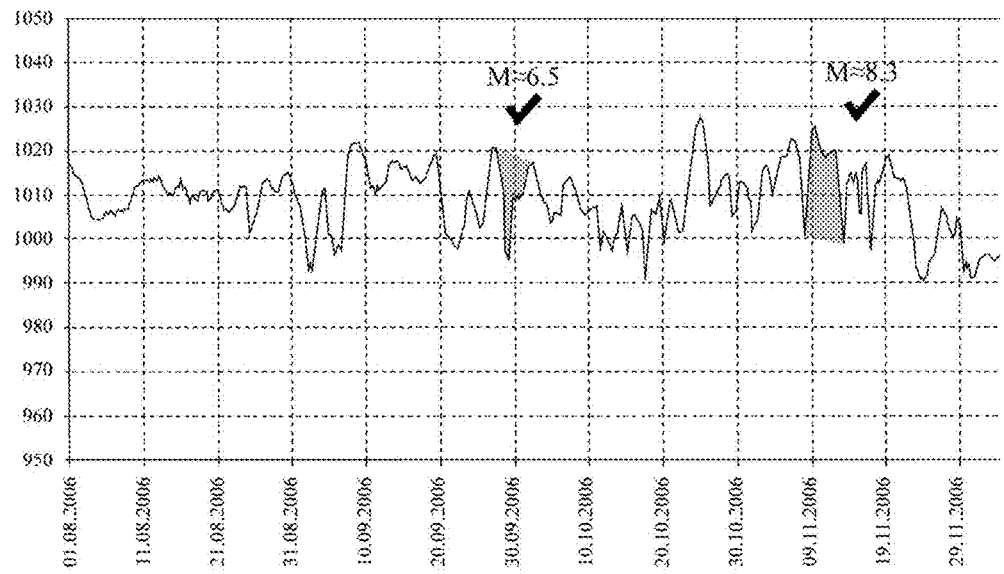
FIG. 14A. Atmospheric pressure over time in the zone of the source of earthquakes in the Central Kuril Islands (Part 1).
Figure 14B:
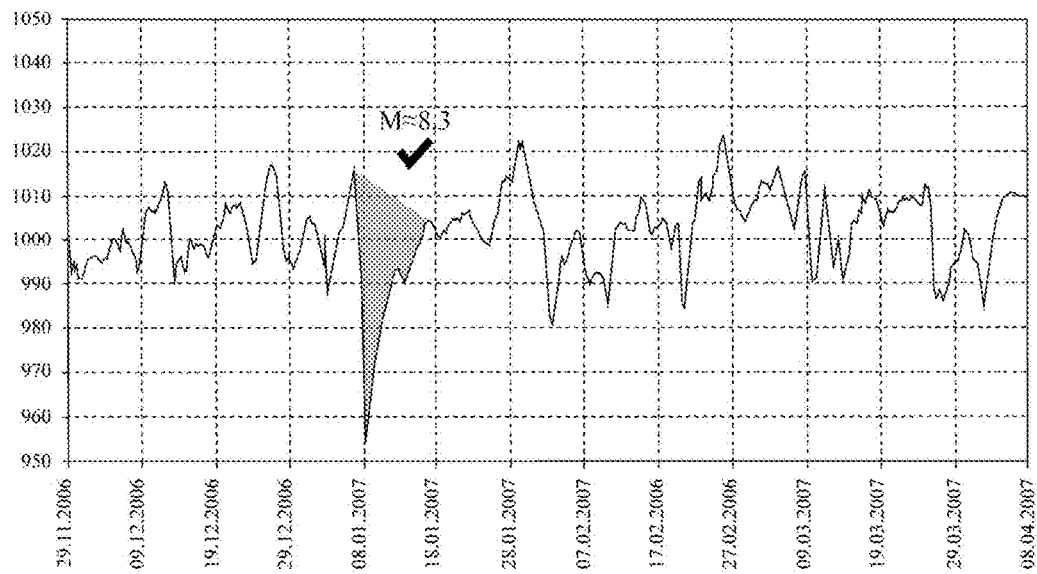
FIG. 14B. Atmospheric pressure over time in the zone of the source of earthquakes in the Central Kuril Islands (Part 2).

The present invention further reveals how strongly sharp fluctuations of the atmospheric pressure over seismic focal points impact the occurrence of relatively weak (i.e., M>4.0-6.0) earthquakes. The powerful aftershock on Jan. 12, 2007 (M≈8.3) of the earthquake on the Central Kuril Islands, which occurred on Nov. 15, 2006 (M≈8.3) had a relation to a sharp change in atmospheric pressure, which, in turn, was linked to a distinctive trigger point in the Earth-Moon-Sun system (see FIGS. 14A and 14B for an illustration of recorded information, showing trigger points due to a significant drop in atmospheric pressure).

Sporadic accumulation and stress relief manifest phase transformations in the lithosphere under the impact of internal and external factors. Phase transformations in macro-systems are analogous to quantum jumps in the microcosm.

The use of the "entropy" model for assessment of the energy potential of seismic focal points, consideration for trigger points in the Earth-Moon-Sun system and fluctuations of the atmospheric pressure, taking into account the energy exchange processes in the lithosphere after strong seismic events in different focal point areas, is the general scheme for short-to-medium period forecasting of major and relevant seismic events according to the present invention.

With the thermodynamic approach, the nature of the stress source in the Earth's crust is not critical. Conventional seismo-geological research helps explain the stress relief mechanisms after an event and also to perform seismic zoning (for longer-period forecasts), but the methods do not ensure medium or short-period forecasting.

Excessive stress in the Earth's crust (i.e. lithosphere) comes from internal (i.e. endogenous) sources within the Earth's cosmic body.

There is a prerequisite for stress relief (i.e. an earthquake), which is that the stress level in the seismic focal point area is close to (i.e. approaching) the limit of the energy capacity (i.e. strength) of the rock portion of the Earth in the focal point zone.

In order to secure the seismic focal point actuation, stress relief in the form of an earthquake—additional external (i.e. exogenous) factors are often necessary. Such factors are the gravitating impact of astronomical bodies (the Moon, the Sun, the Earth, and respective barycentres between two or more of the bodies) and atmospheric pressure fluctuations (in particular, a significant drop of atmospheric pressure), both of which are utilized by the present invention to better predict, in the medium to short term, the occurrence of upcoming and/or imminent seismic events. Other factors exist, but gravitational effects are the main focus of the present invention in relation to stress relief in the Earth's crust and detection/prediction thereof.

Figure 15:
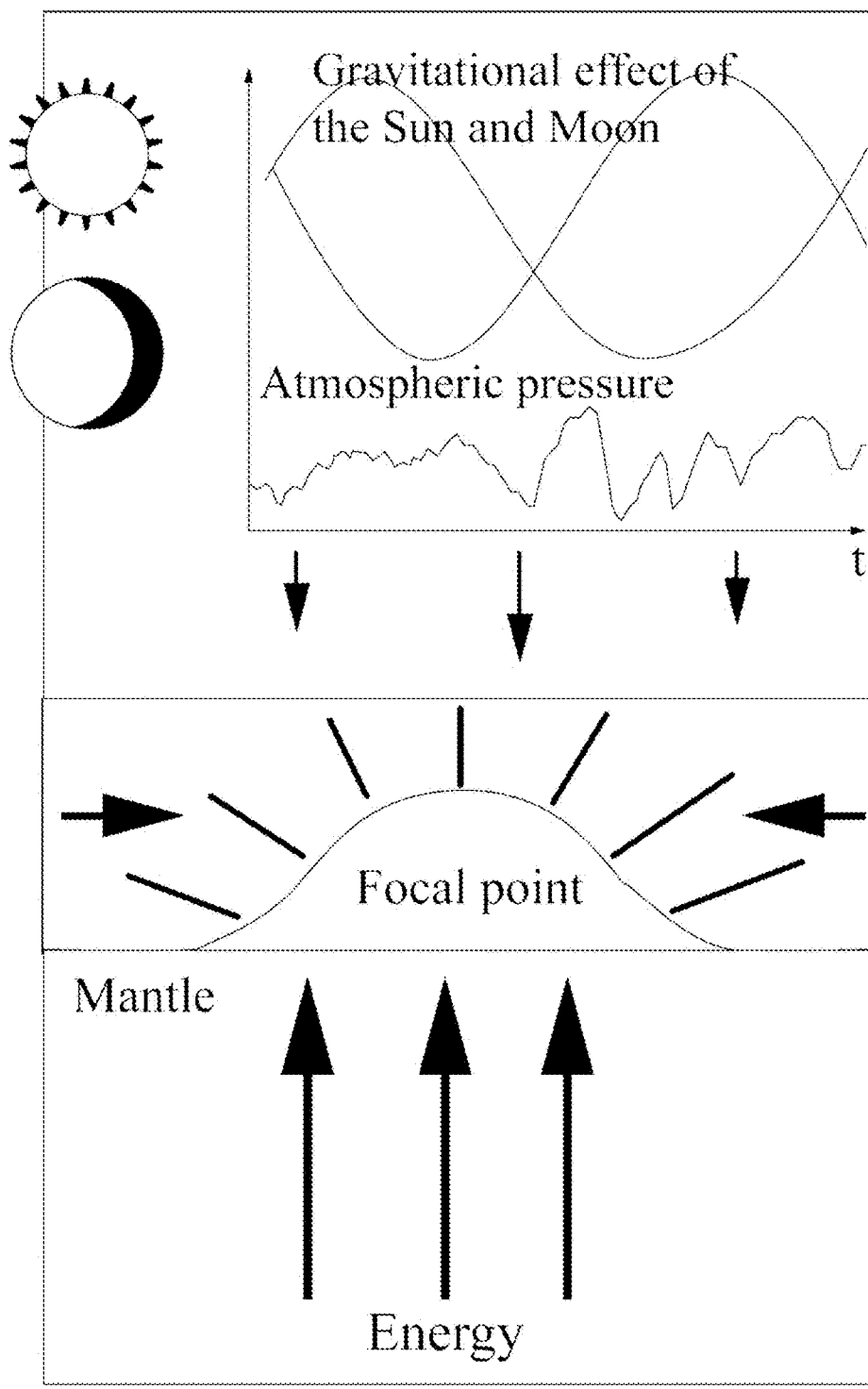
FIG. 15. A model of the accumulation of stress and stress relief in the Earth's crust (lithosphere).
Figure 16:
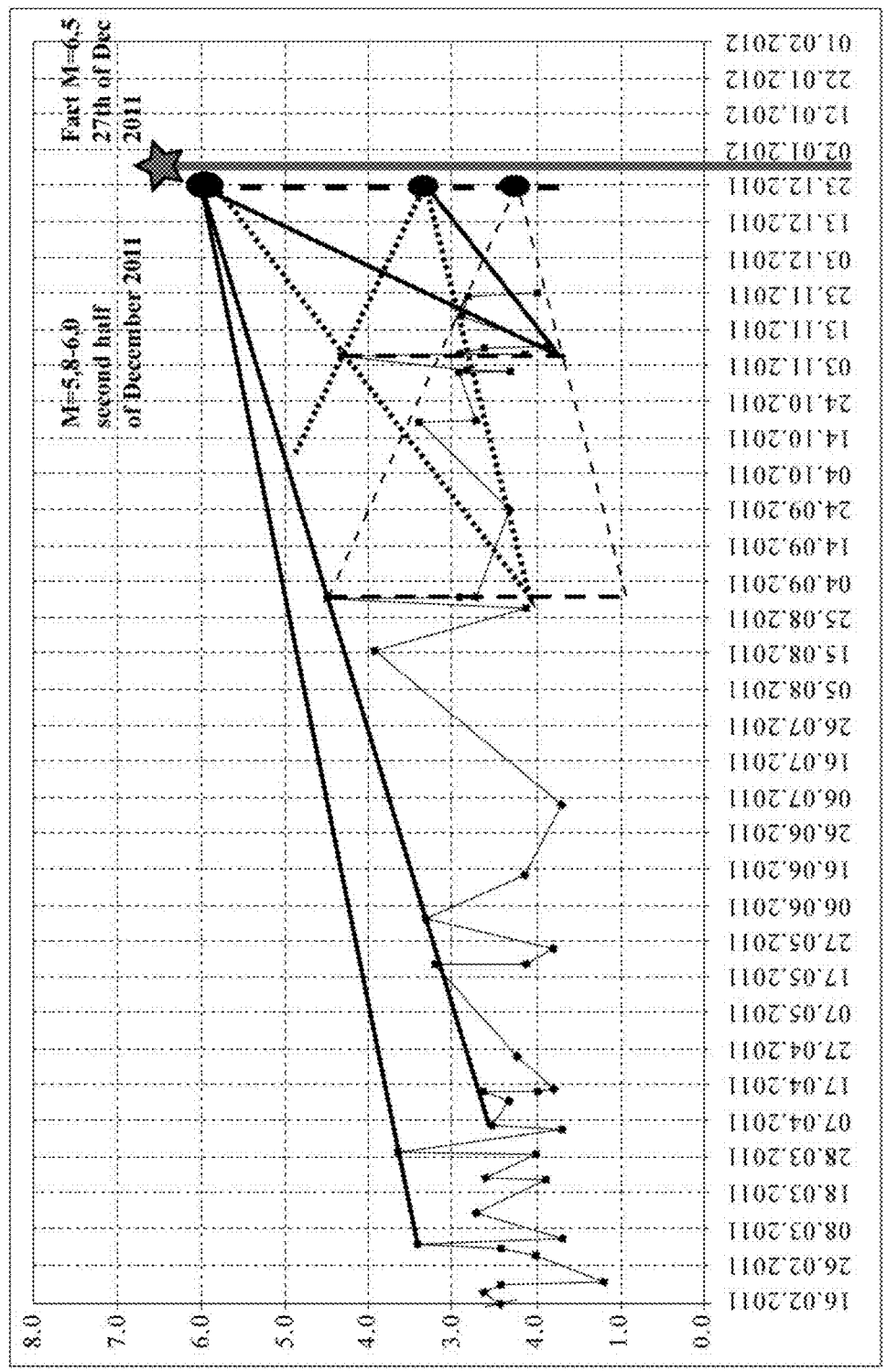
FIG. 16. An example of an earthquake forecast in Kamchatka, according to the present invention.
Figure 17:
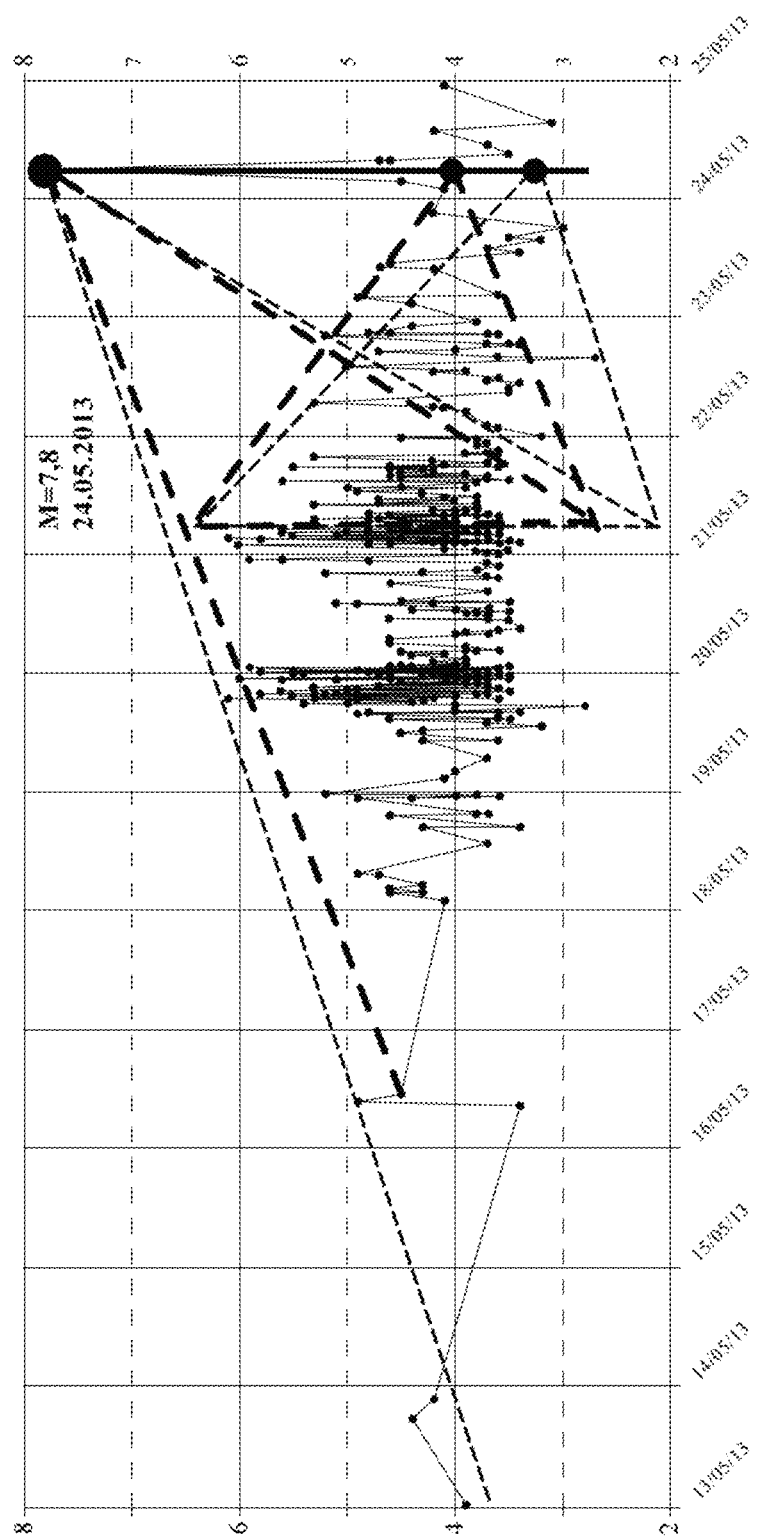
FIG. 17. An example of an earthquake forecast for the Sea of Okhotsk, according to the present invention.
Figure 18:
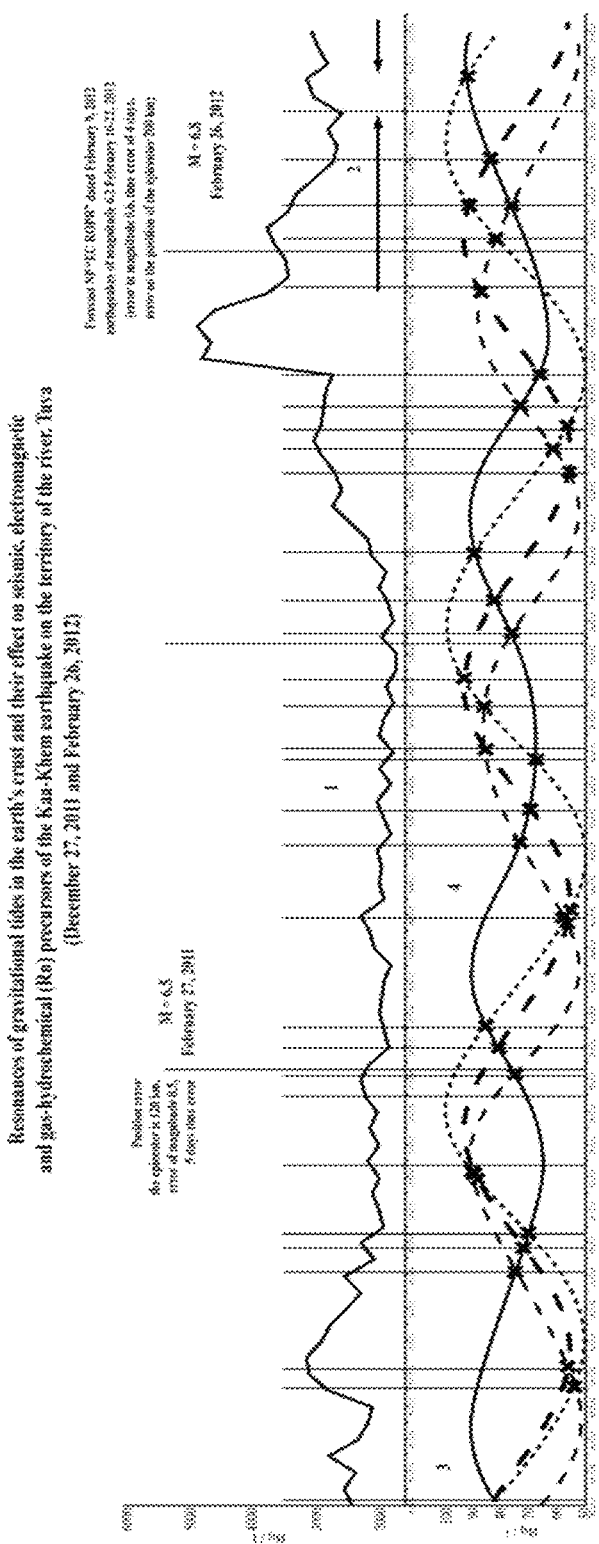
FIG. 18. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 1).
Figure 19:
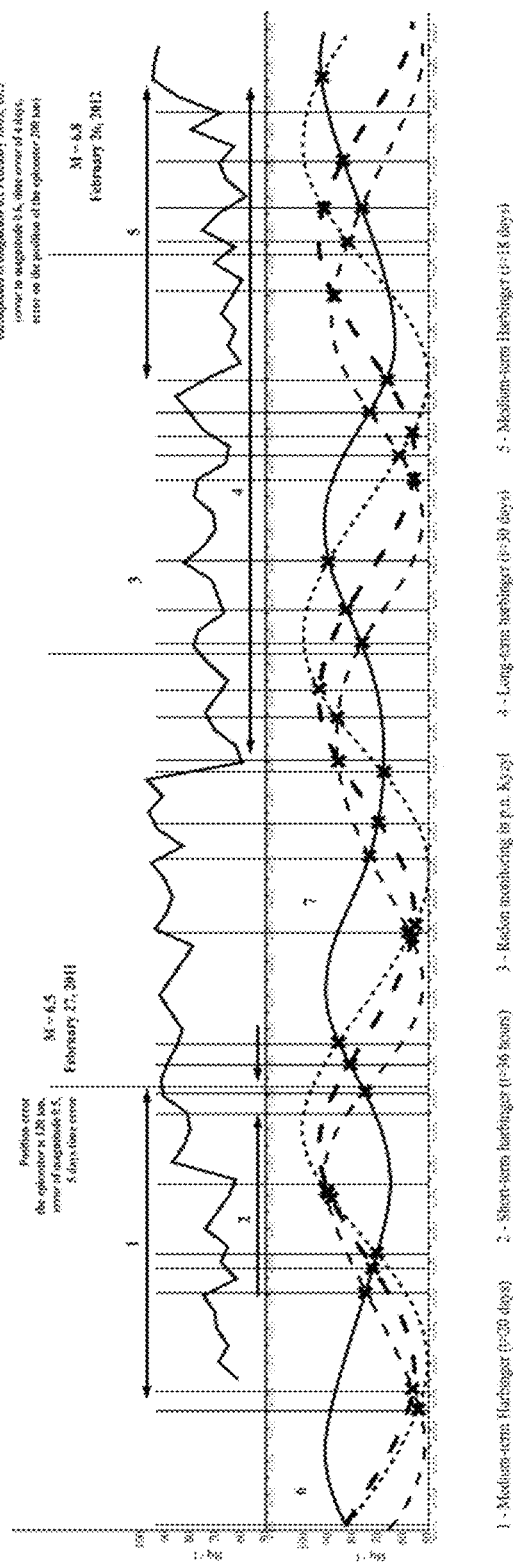
FIG. 19. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 2).
Figure 20:
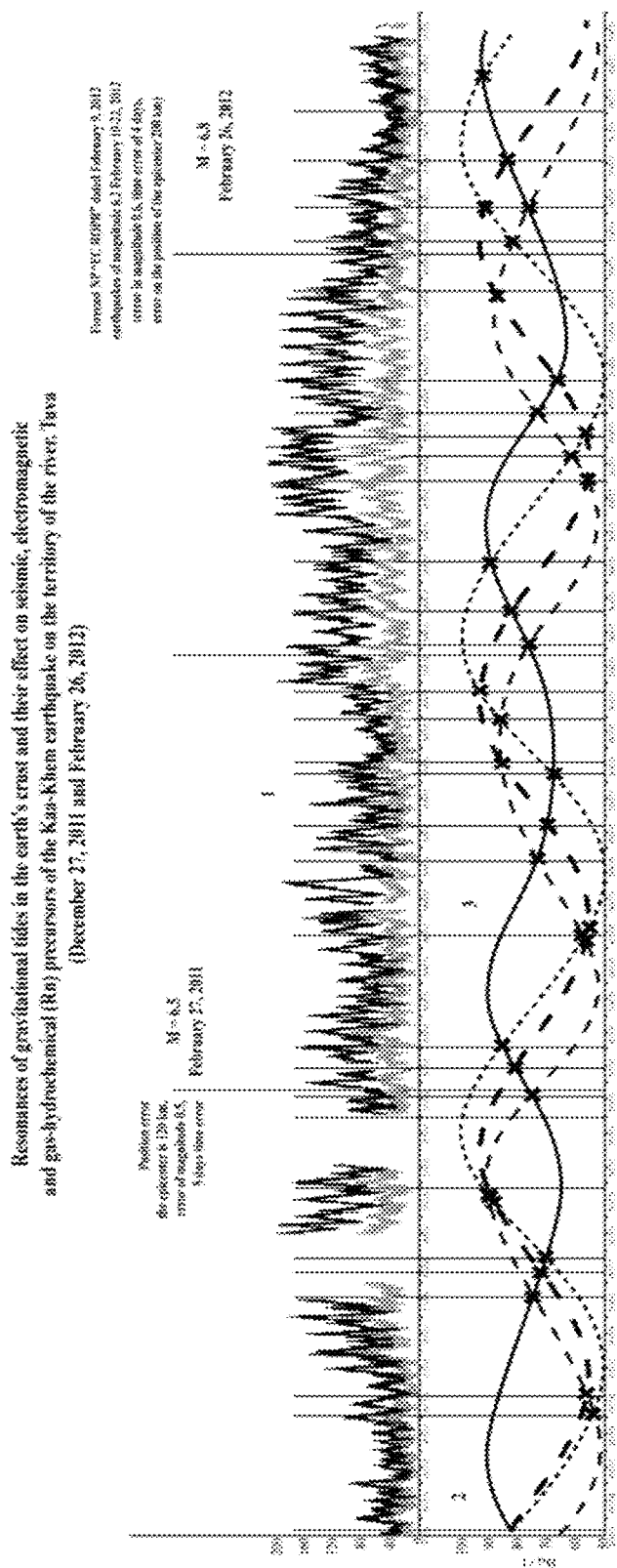
FIG. 20. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 3).
Figure 21:
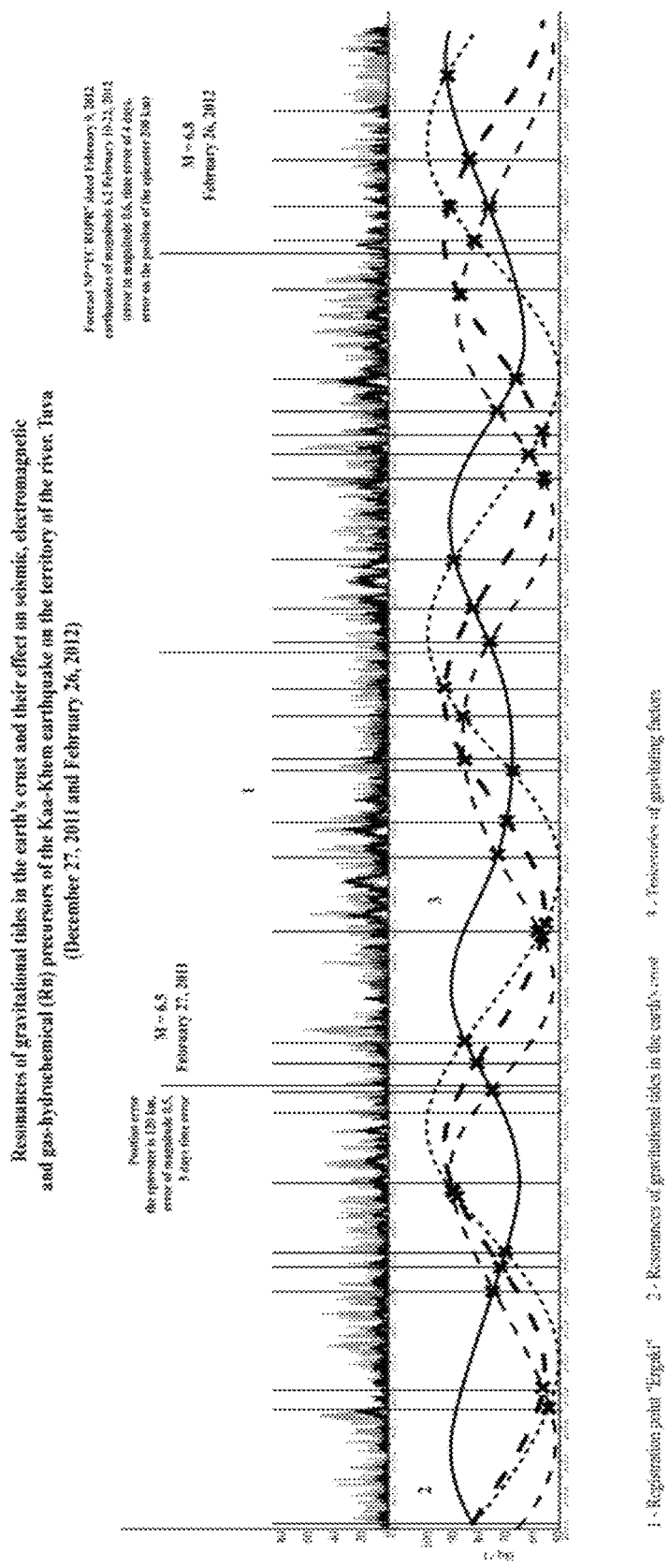
FIG. 21. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 4).
Figure 22:
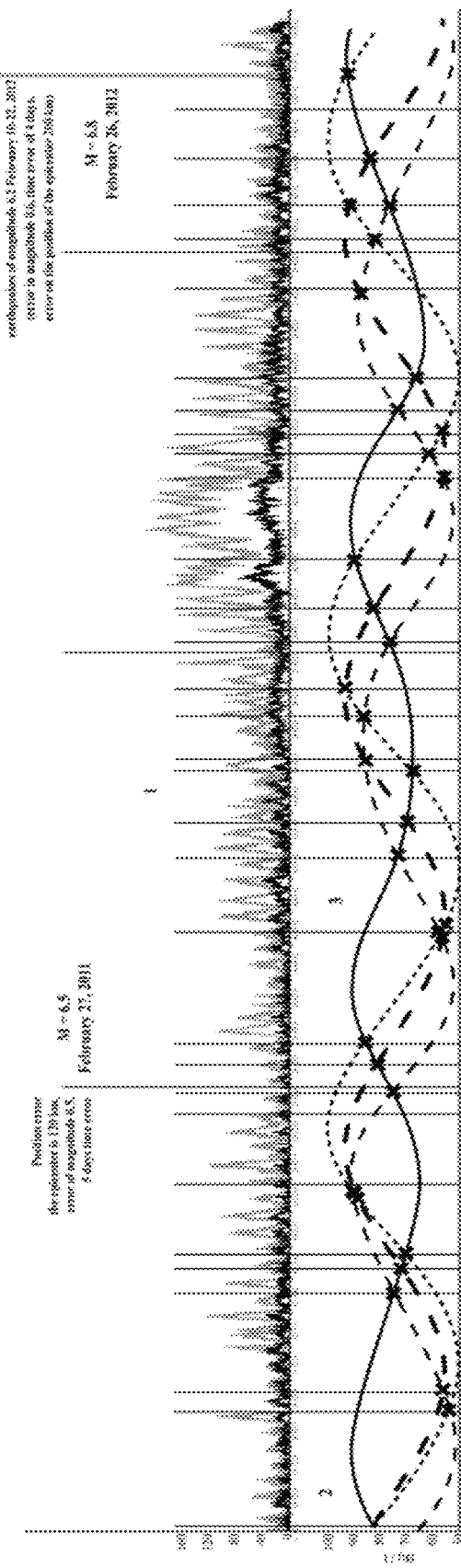
FIG. 22. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 5).
Figure 23:
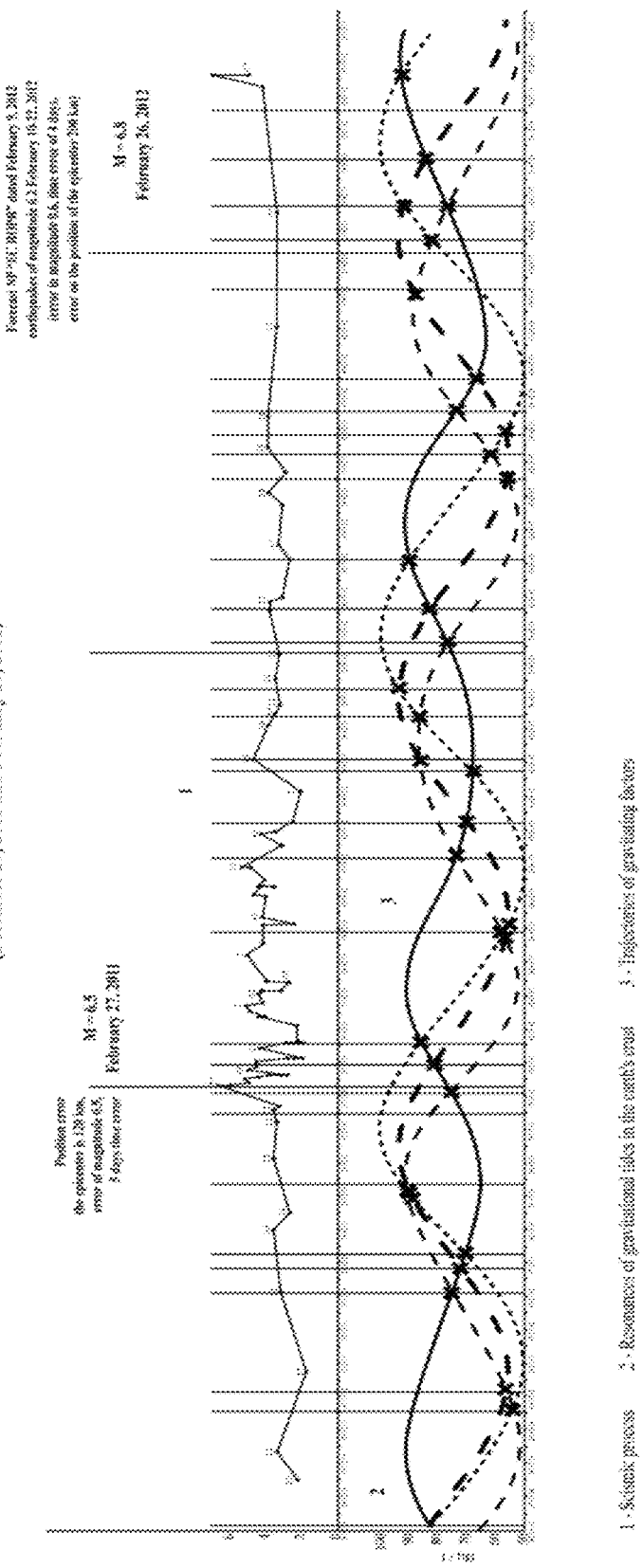
FIG. 23. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 6).
Figure 24:
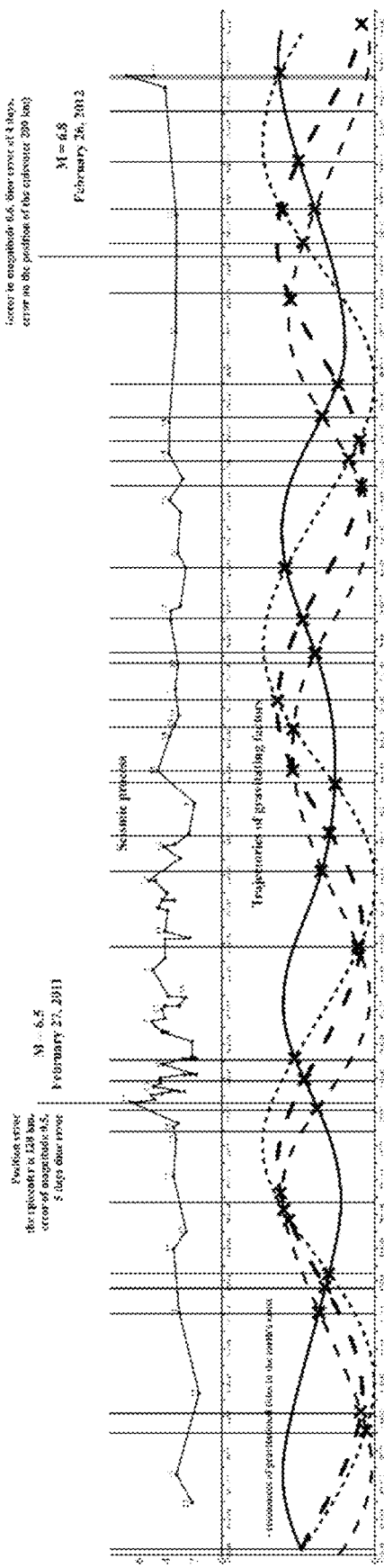
FIG. 24. Resonances of gravitational tides in the Earth's crust and their effect on seismic, electromagnetic, and gas-hadrochemical (Rn) precursors of the Kaa-Khem earthquake, on the territory of the Tuva River (Dec. 27, 2011, and Feb. 26, 2012) (Part 7).
Figure 25:
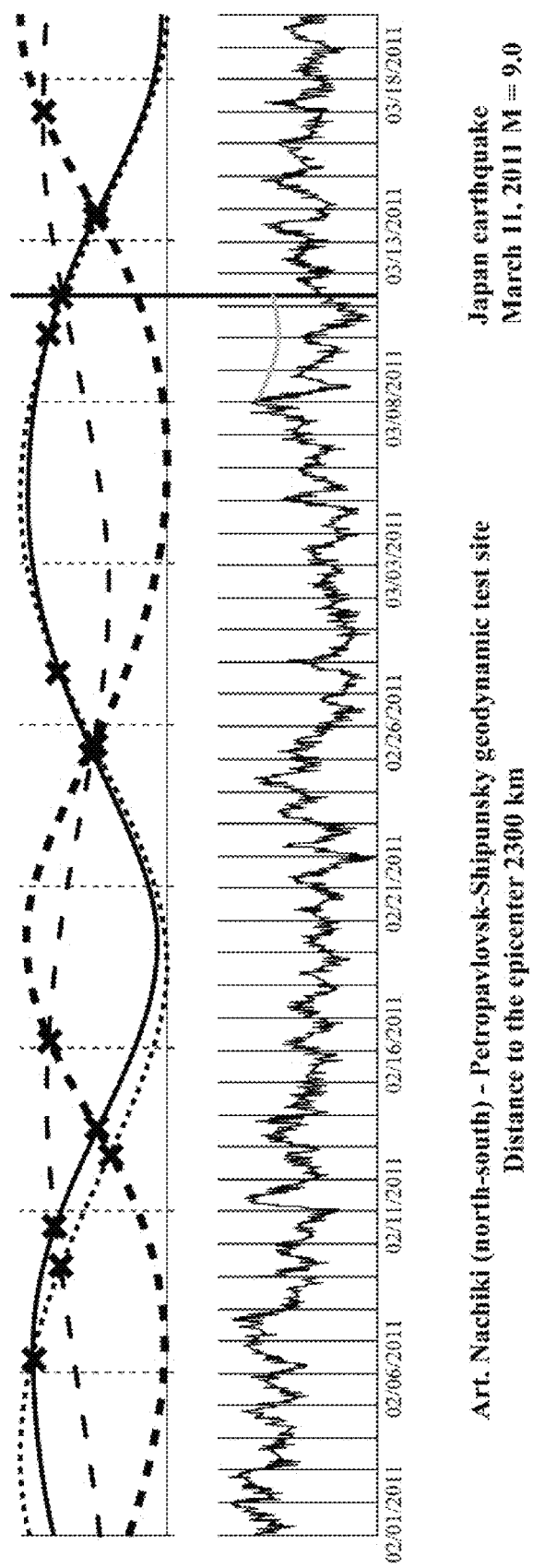
FIG. 25. The relationship of the Japanese earthquake of Mar. 11, 2011, with the moments of gravitational resonances. Part 1.
Figure 26:
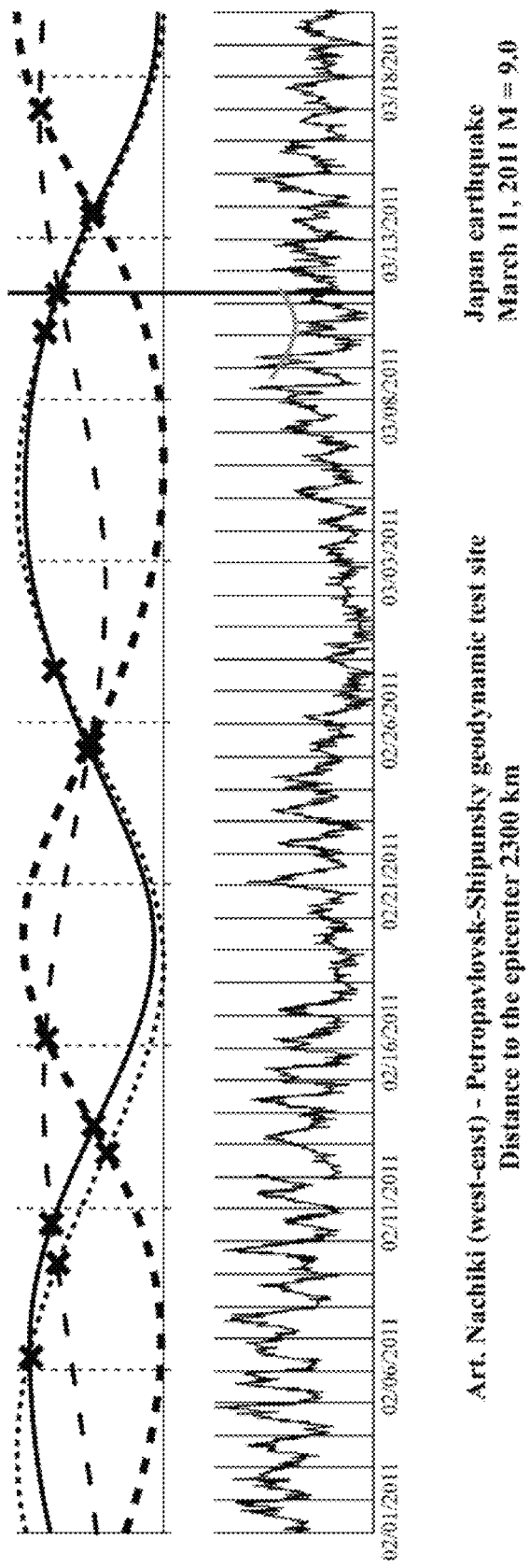
FIG. 26. The relationship of the Japanese earthquake of Mar. 11, 2011, with the moments of gravitational resonances. Part 2.
Figure 27:
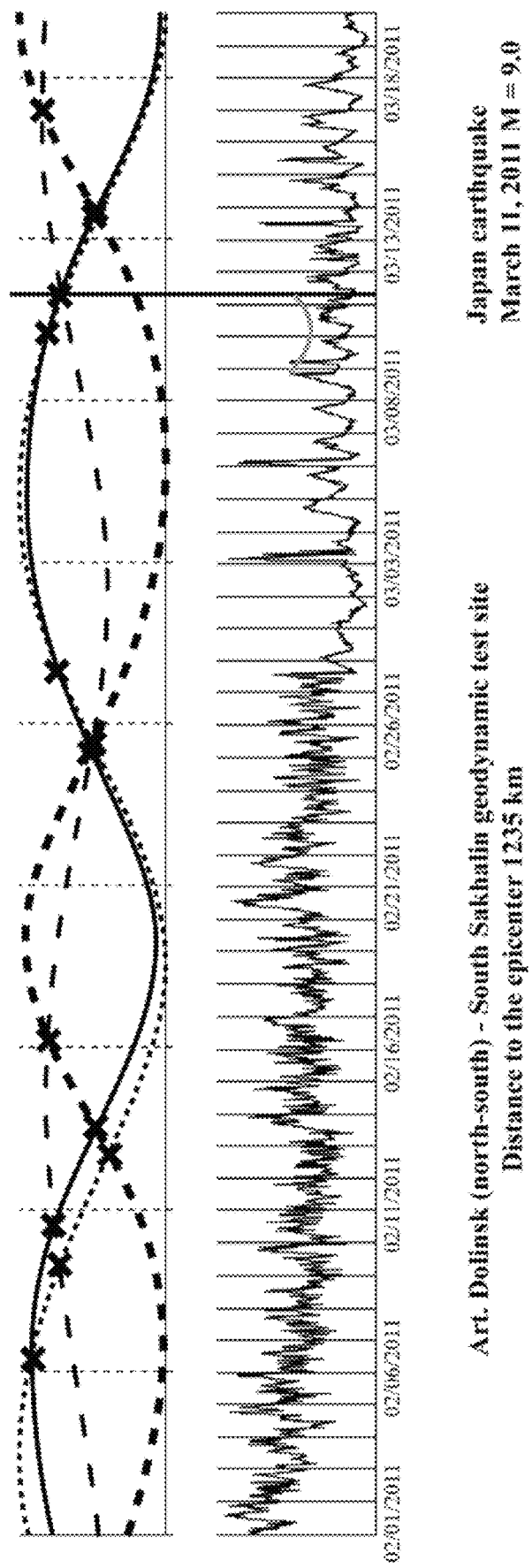
FIG. 27. The relationship of the Japanese earthquake of Mar. 11, 2011, with the moments of gravitational resonances. Part 3.
Figure 28:
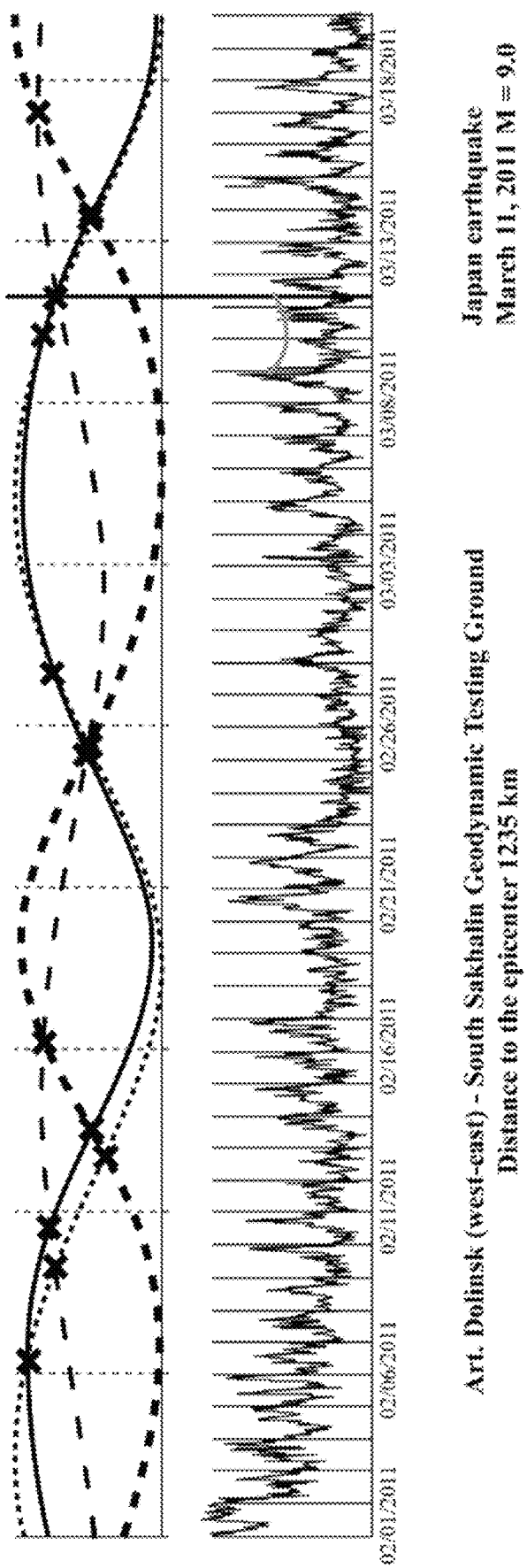
FIG. 28. The relationship of the Japanese earthquake of Mar. 11, 2011, with the moments of gravitational resonances. Part 4.
Figure 29:
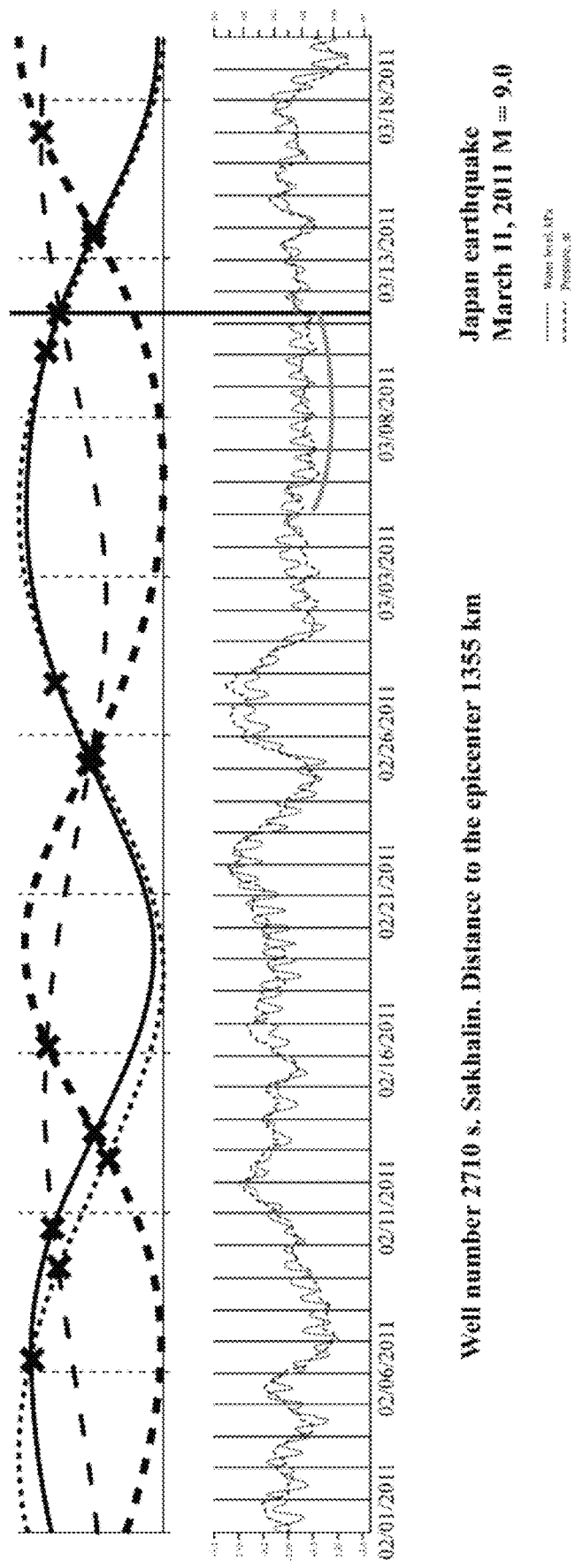
FIG. 29. The relationship of the Japanese earthquake of Mar. 11, 2011, with the moments of gravitational resonances. Part 5.
Figure 30:
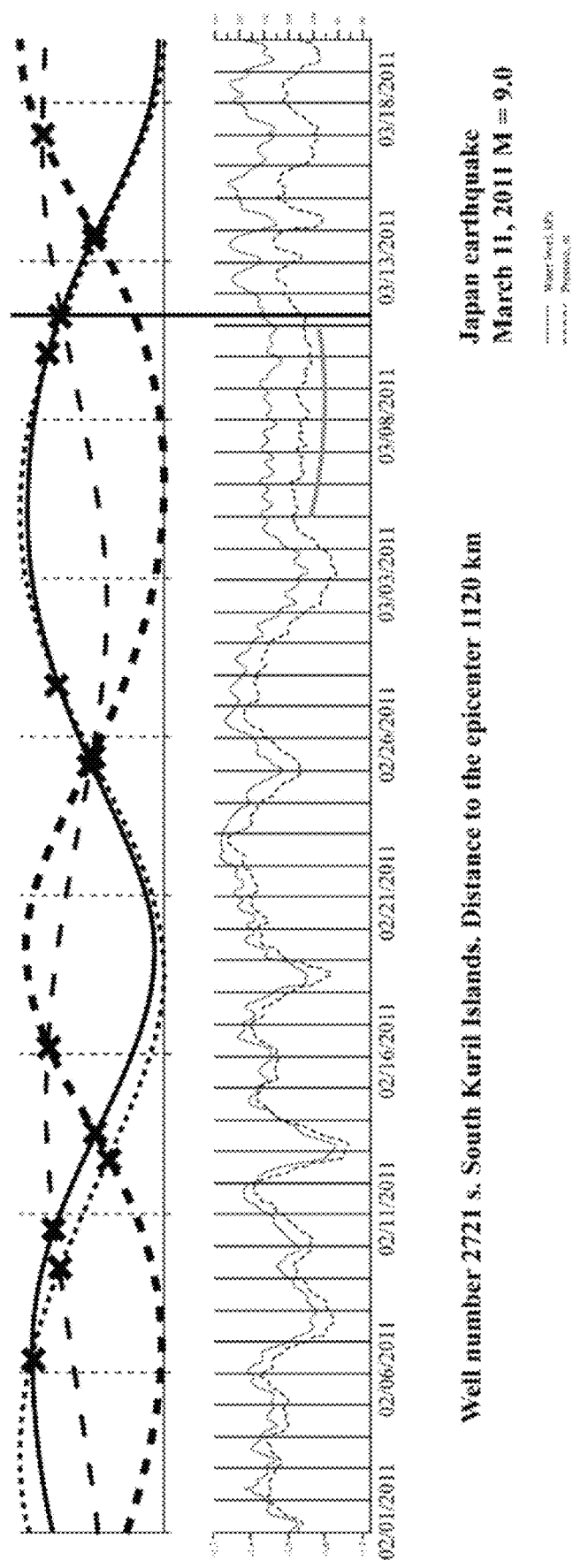
FIG. 30. The relationship of the Japanese earthquake of Mar. 11, 2011, with the moments of gravitational resonances. Part 6.
Figure 31:
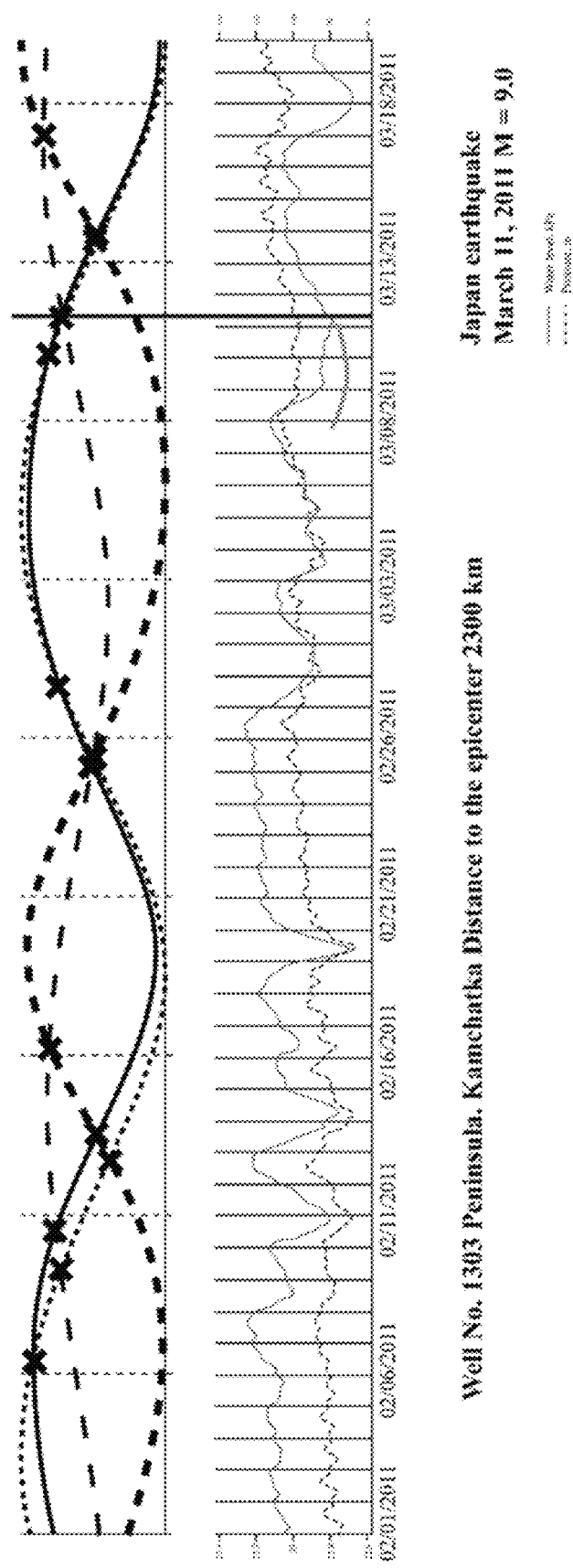
FIG. 31. The relationship of the Japanese earthquake of Mar. 11, 2011, with the moments of gravitational resonances. Part 7.
Figure 32:
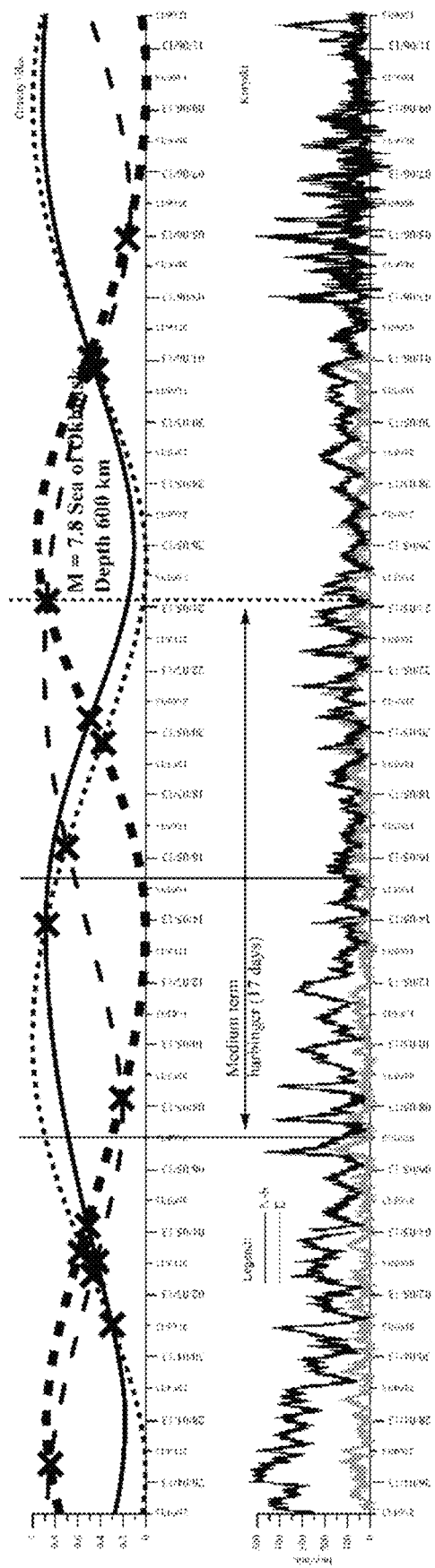
FIG. 32. The relationship of the earthquake in the Okhotsk Sea (May 21, 2013) with the moments of gravitational resonances. Part 1.
Figure 33:
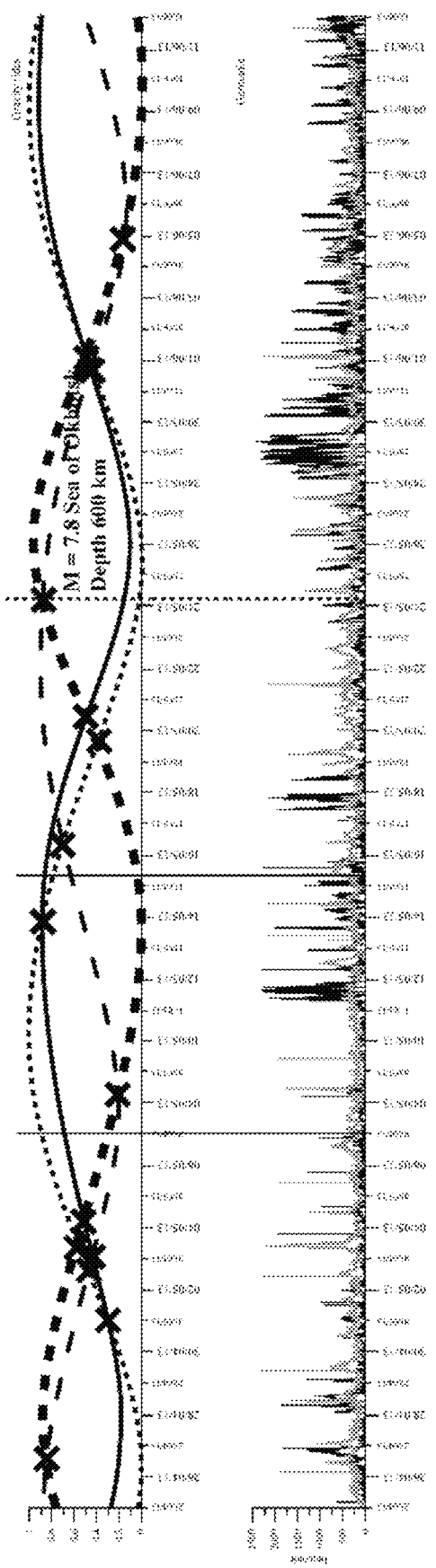
FIG. 33. The relationship of the earthquake in the Okhotsk Sea (May 21, 2013) with the moments of gravitational resonances. Part 2.
Figure 34:
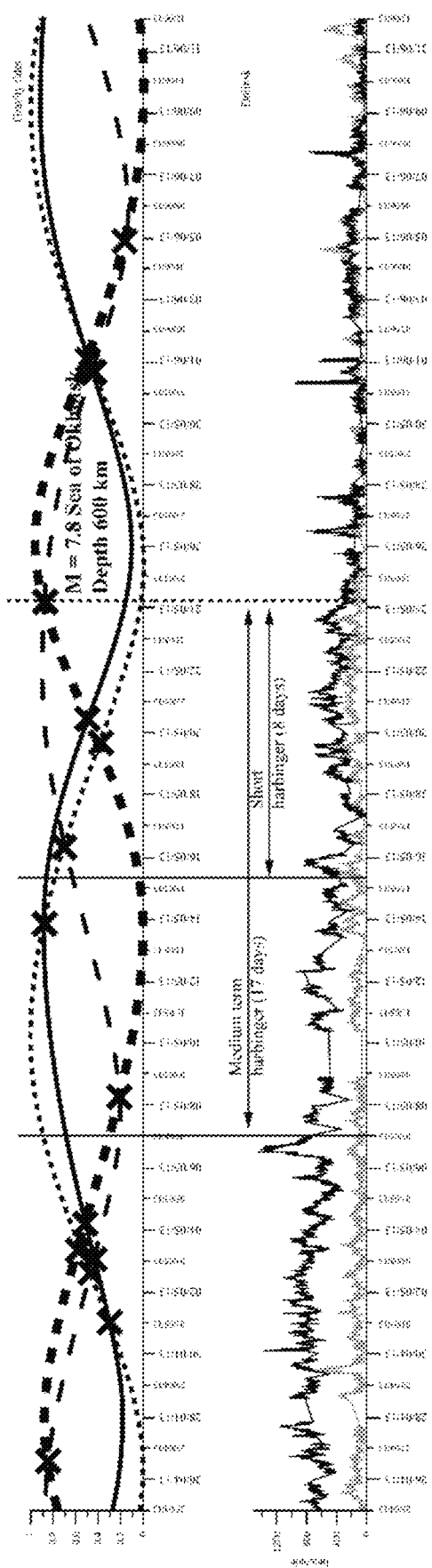
FIG. 34. The relationship of the earthquake in the Okhotsk Sea (May 21, 2013) with the moments of gravitational resonances. Part 3.
Figure 35:
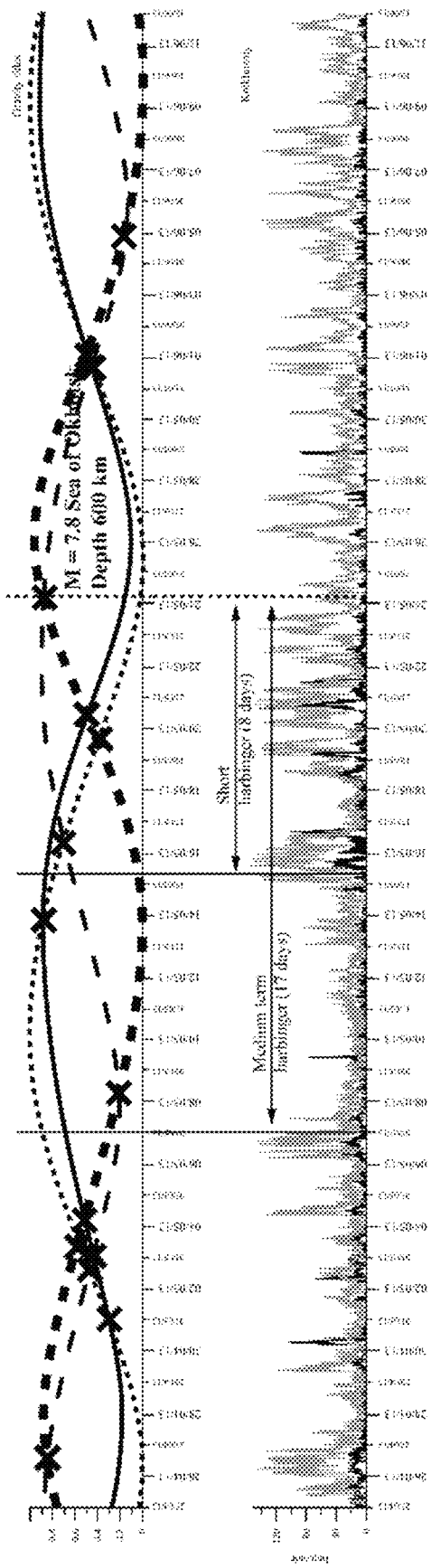
FIG. 35. The relationship of the earthquake in the Okhotsk Sea (May 21, 2013) with the moments of gravitational resonances. Part 4.
Figure 36:
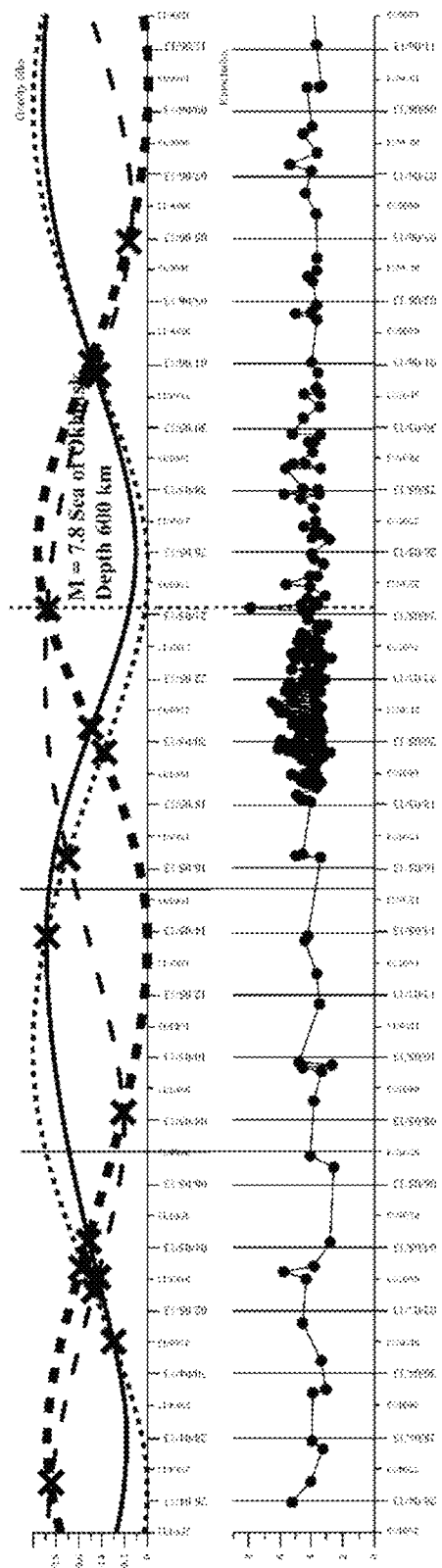
FIG. 36. The relationship of the earthquake in the Okhotsk Sea (May 21, 2013) with the moments of gravitational resonances. Part 5.
Figure 37:
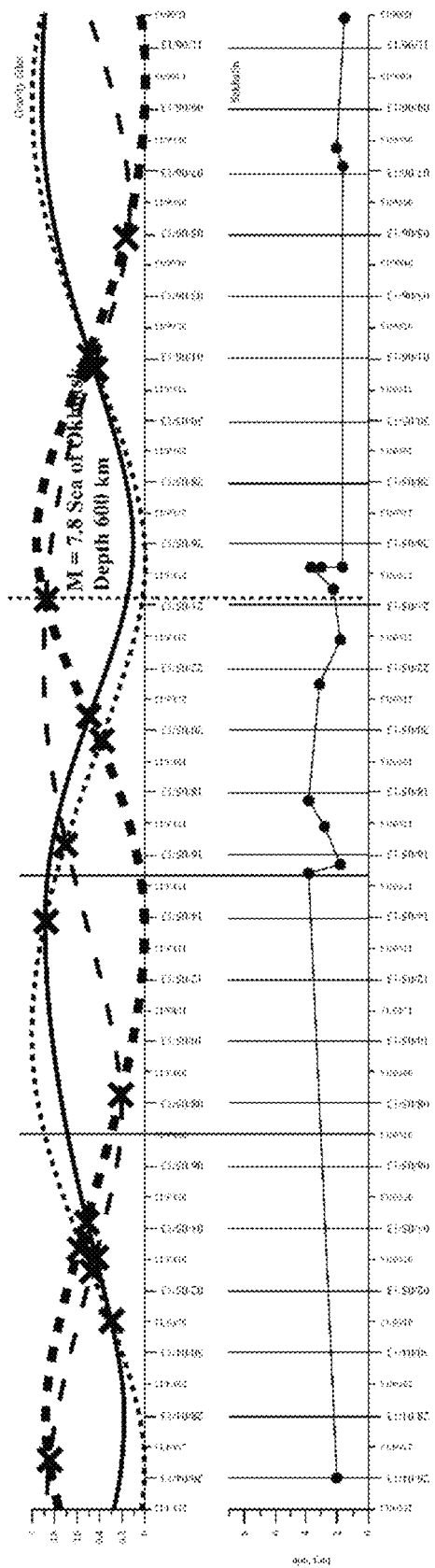
FIG. 37. The relationship of the earthquake in the Okhotsk Sea (May 24, 2013) with the moments of gravitational resonances. Part 6.
Figure 38:
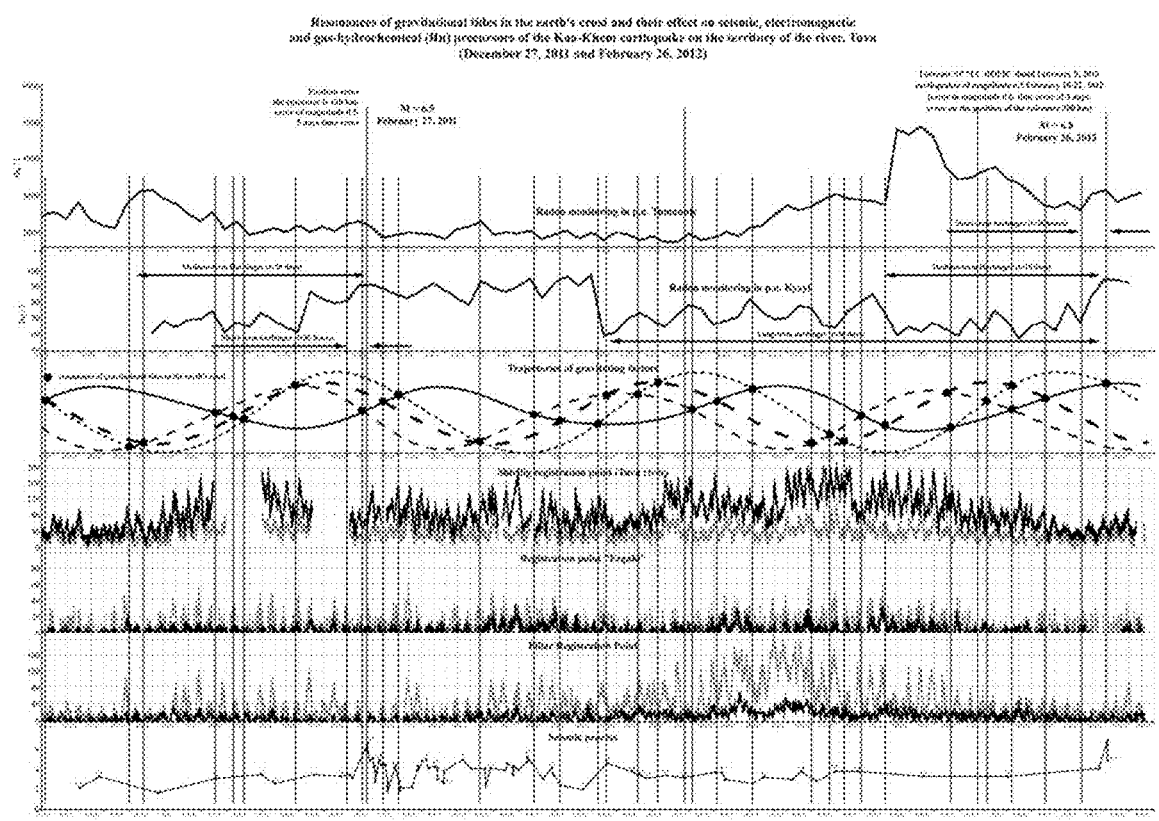
FIG. 38. Resonances of gravitational tides in the earth's crust and their effect on seismic, electromagnetic, and gas-hadrochemical (Rn) precursors of the Kaa-Khem earthquake on the territory of the Tuva River (Dec. 27, 2011, and Feb. 26, 2012). A general drawing.
Figure 39:
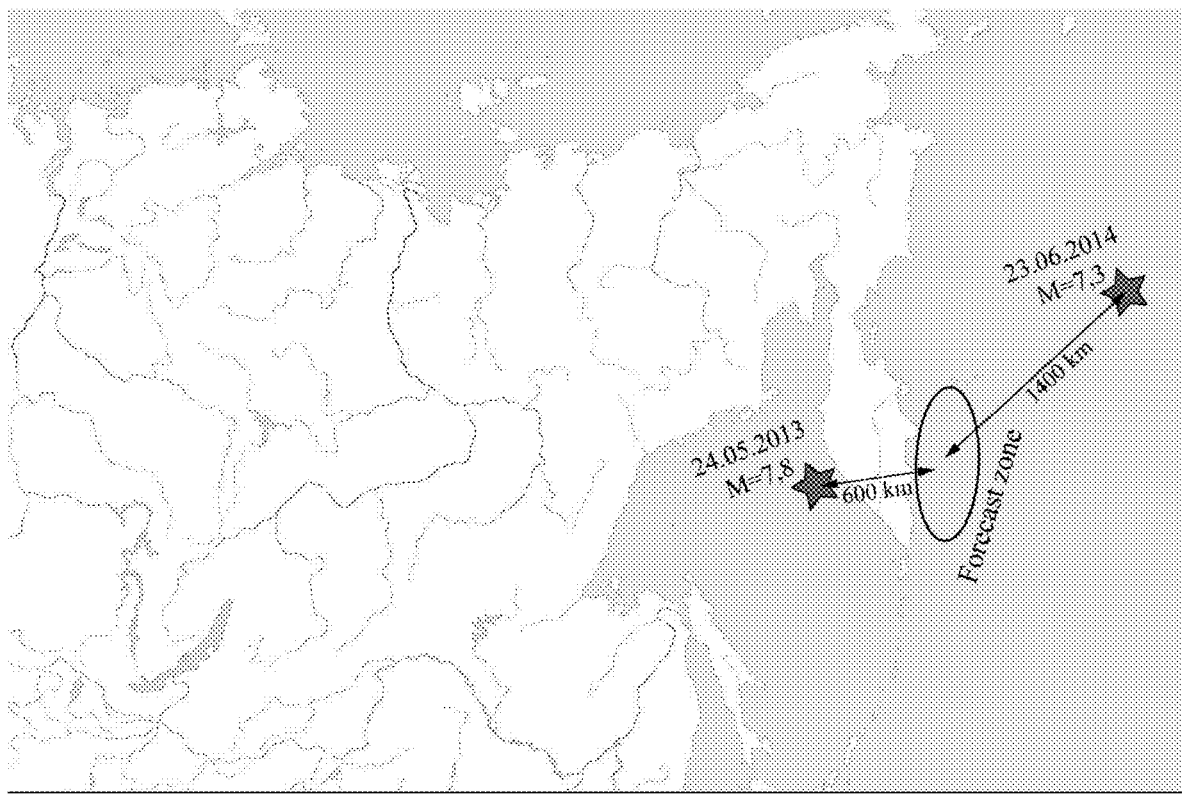
FIG. 39. A map view of the earthquake in the Okhotsk Sea (May 24, 2013).
Figure 40:
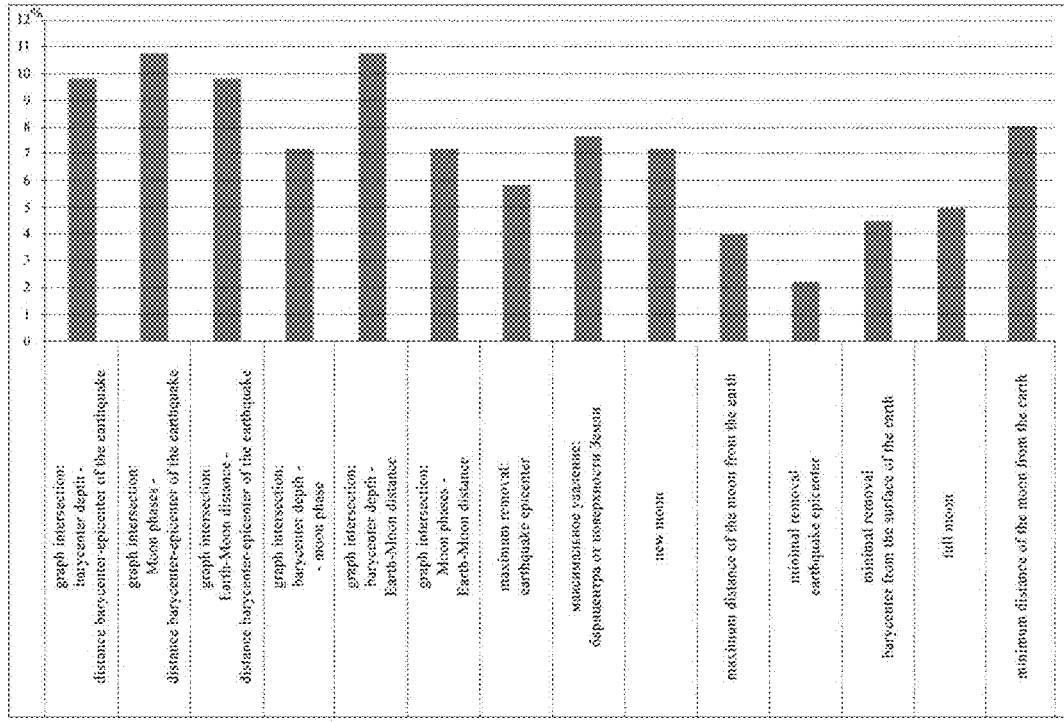
FIG. 40. Frequency distribution of the moments of strong earthquakes (M>6) in the 20-21st centuries, showing a number of different types of resonances of gravitational tides (evidence of correlation).
Figure 41:
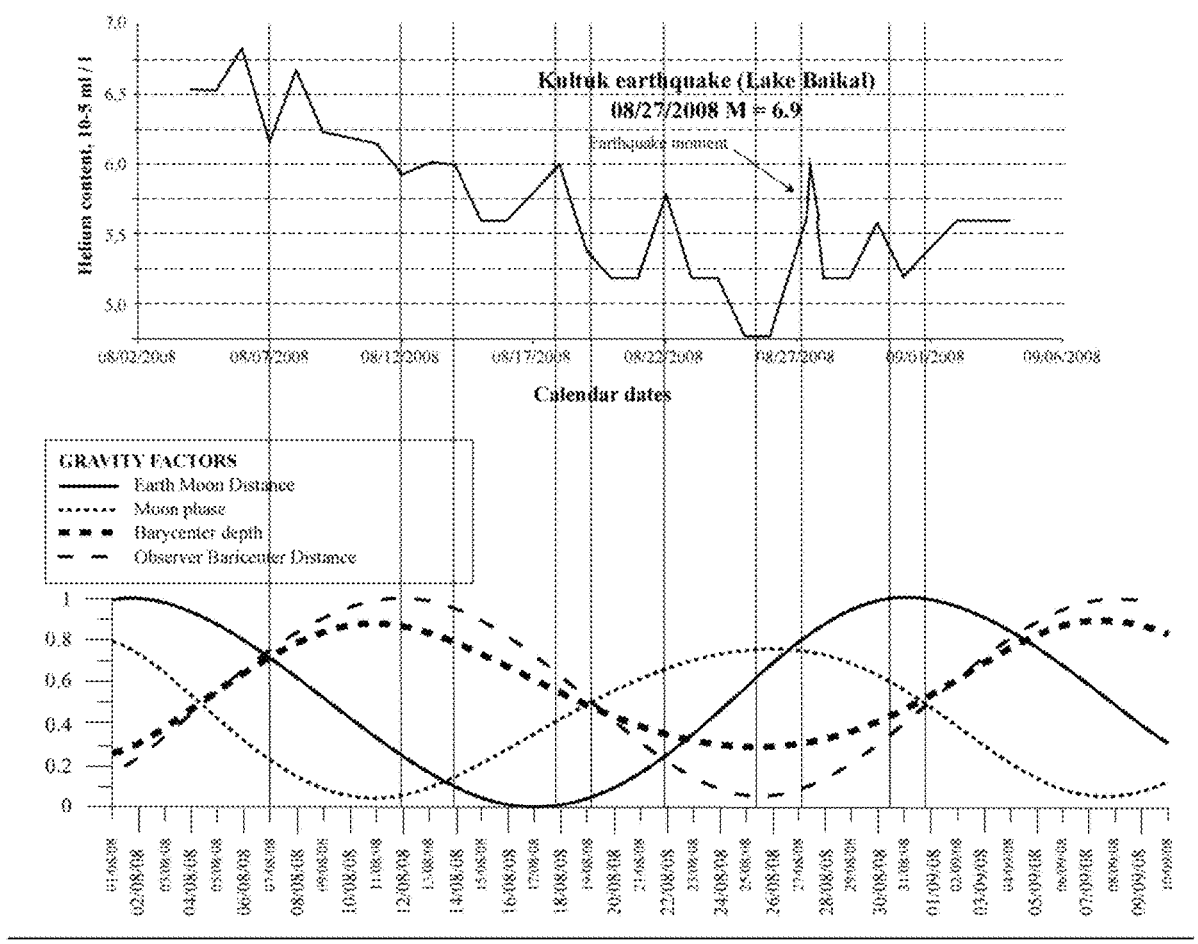
FIG. 41. Schedule of helium emission in lake water, Baikal.
Figure 42:
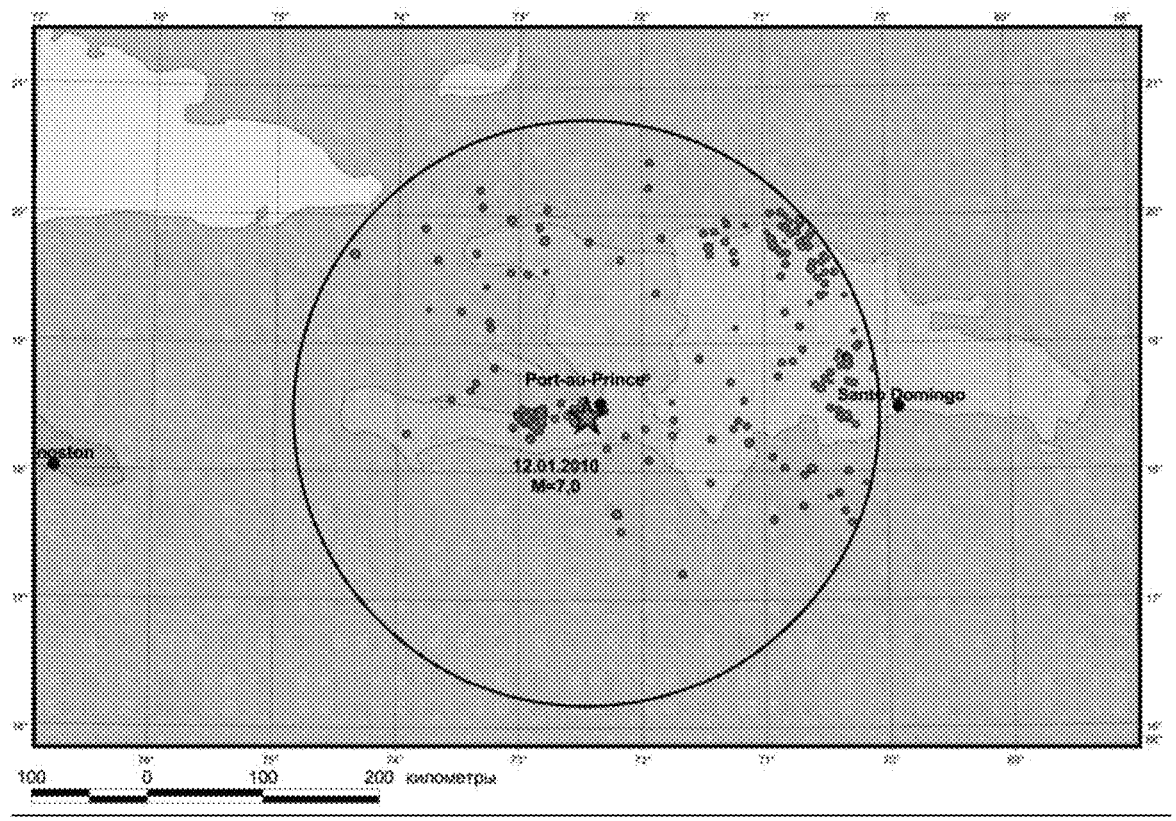
FIG. 42. Haiti earthquake, map view, Jan. 12, 2010.
Figure 43:
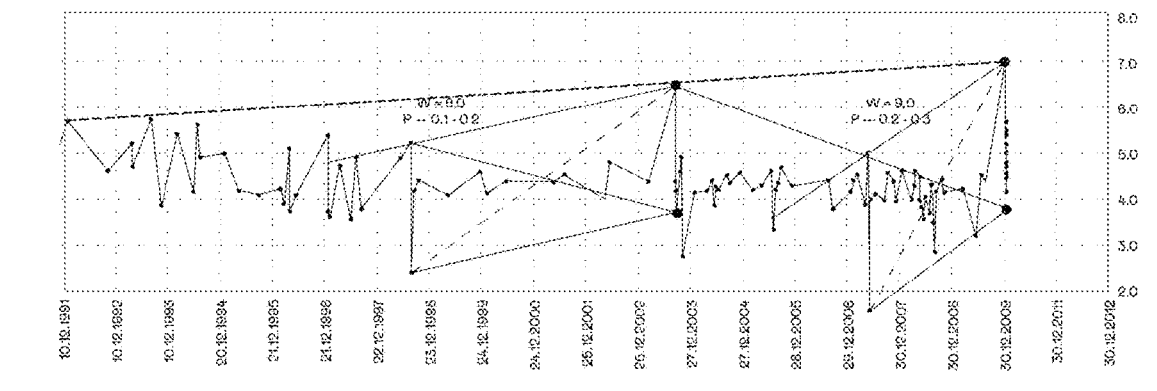
FIG. 43. A retroforecast of the Haiti earthquake, Jan. 12, 2010, according to the present invention.
Figure 44:
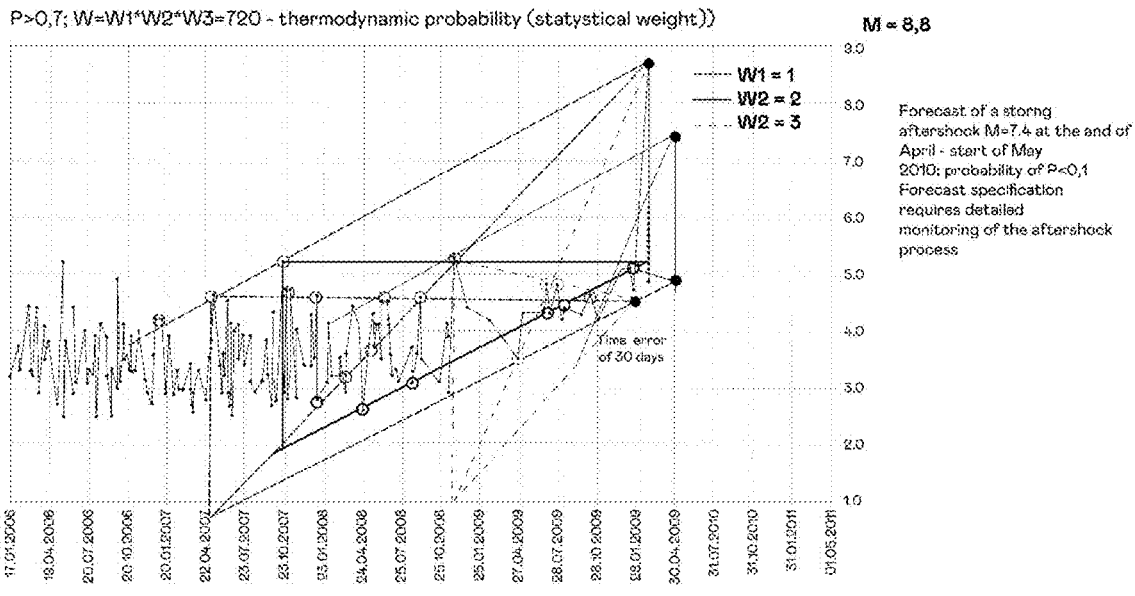
FIG. 44. A retroforecast of the Chilean earthquake, Feb. 27, 2010, according to the present invention.
Figure 45:
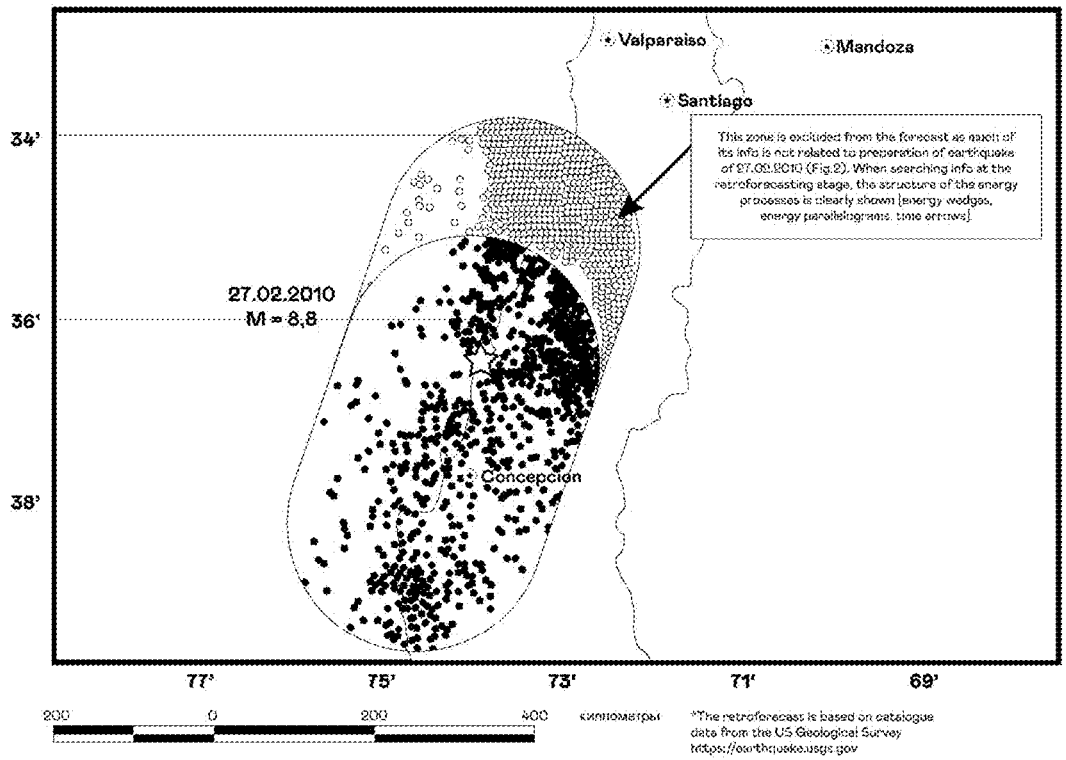
FIG. 45. A map view of the Chilean earthquake, Feb. 27, 2010.

A general model of accumulation and stress relief in the Earth's crust (i.e. lithosphere) can be presented in the form shown in FIG. 15. FIG. 15 illustrates the various forces which act upon a focal point within or along the Earth's surface: forces due to the gravitational pull from points in the Earth-Moon-Sun system, the force of atmospheric pressure, forces from the ground on either side of the focal point, pressure from inside the focal point, and forces from the Earth's core. The combination of these forces are measured as the energy (E) of the focal point.

Based on the analysis of global and regional seismic monitoring data within the zones with abnormally powerful energy processes, it is necessary to detect energy wedges and assess their parameters according to the solutions presented here.

It is advisable to consider potential trigger points based on the analysis of the Moon-Sun system positions and irregularities in the atmospheric pressure (e.g., the ionosphere condition) of the seismic focal point area. Conventional registration of the seismo-geological information about a potentially dangerous seismic focal point zone is necessary too.

The algorithm presented above enables one to make forecasts of seismic events 1-3 months in advance (a medium-period forecast) and also forecasts 1-10 days (short-period forecasts) of acceptable reliability (i.e. at least 75% accurate).

The input data for the earthquake prediction algorithm may be provided by seismographs, which are capable of measuring oscillation frequencies from zero Hz to 100 Hz. As a nonlimiting example, seismographs of the Baikal SME-4311 line and their analogs, SK1-P, SM3-KV, and various known velocimeters and accelerometers may be used. Additional examples include Guralp 5 and 6 Series seismometers.

To summarize the novelty of the invention, the present technology is capable of predicting earthquakes with an accuracy of 70-80%. The technology is based on data collected from 300 earthquakes over 15 years. No currently known model provides for such accuracy; moreover, other medium-term and short-term models do not currently exist whatsoever (i.e. predicting within a few months to days the onset of seismic activity).

The entropy model presented above is also novel and has previously never been used with respect to the detection and/or prediction of seismic events. Therefore, the algorithm disclosed above, which is based on the entropy model, is a novel approach to earthquake prediction.

Accuracy can be enhanced with a network of seismic stations set up in compliance with requirements below; data from local seismometers (registering minor earthquakes with magnitude of under 3), as this data is unavailable in open source catalogs; a network of radon gas analyzers in place and information from them being available; and online information about infrared radiation (from a satellite) on the forecast dates of the anomaly analysis.

Typical Requirements Forming a User's Network of Seismic Stations for Forecasting The following data collection systems are required to study in-depth and velocity structure.

1. A detailed data collection system with a large number of stations (e.g., 100, 1,000, 10,000 stations) distributed throughout an observation area, each station being about 2-20 km from any other station.

2. A data collection method/system, comprising:

a) providing the territorial location of the seismic stations evenly distributed throughout the observation zone, with an "average distance between stations" of 10-15 km, preferably 10 km (this may be, e.g., a system previously designed for seismic monitoring of local earthquakes);

b) providing a series of profiles, each profile considered for different areas of the study area, primarily according to the trend of the main geological structures, with a distance between stations of 2-5 km, 5-10 km, or 10-15 km, and a distance between profiles of 10-20 km;

c) performing a geodynamic monitoring with inertial seismometers, the inertial seismometers measuring the motion of the ground (i.e., base) in relation to the point of movement of the seismic mass. Inertial seismometers are preferred because they are easier to use and are more sensitive to signals generated by earthquakes.

For seismic monitoring purposes, it is recommended to use short-range sensors of the type, SM-3 KV or SK-1P (CM-3 KB, CK-1H), and a broadband accelerometer of the type, AO531. Short-range geophones measure signals in the range of 0.1-50 Hz with a base frequency of 0.2-1 Hz, thus having stable amplitude-frequency characteristics for the range of frequencies covered by earthquakes.

Finally, after receiving the data collected, the following is performed:

Assess the stress-deformed states of the geo-environment in the area under surveillance;

Scan the forecast area (using, e.g., earthquake catalogs) by means of information cells for various magnitudes of predicted intense seismic events;

Model seismic processes in "magnitude—time" coordinates for each information cell;

Identify energy levels;

Reconstruct low-energy processes (events);

Single out key components in the structure of geodynamic processes, calculate slope angles for maximum and minimum energy levels; assess seismic process intensity ("power level");

Build time arrows in "magnitude—time" coordinates;

Identify real and virtual energy centers controlling the seismic process, which are formed in energy level break points;

Analyze the variability of the parameters above throughout the forecast area; and Report on and update the current seismic situation and upcoming earthquakes.

General Description of the Algorithm for Identifying Seismic Activity Indicators The task of the algorithm is to search for and single out a special data sequence within a time series of seismic events. The data sequence may be regarded as an indicator of a future seismic activity.

Figure 46:
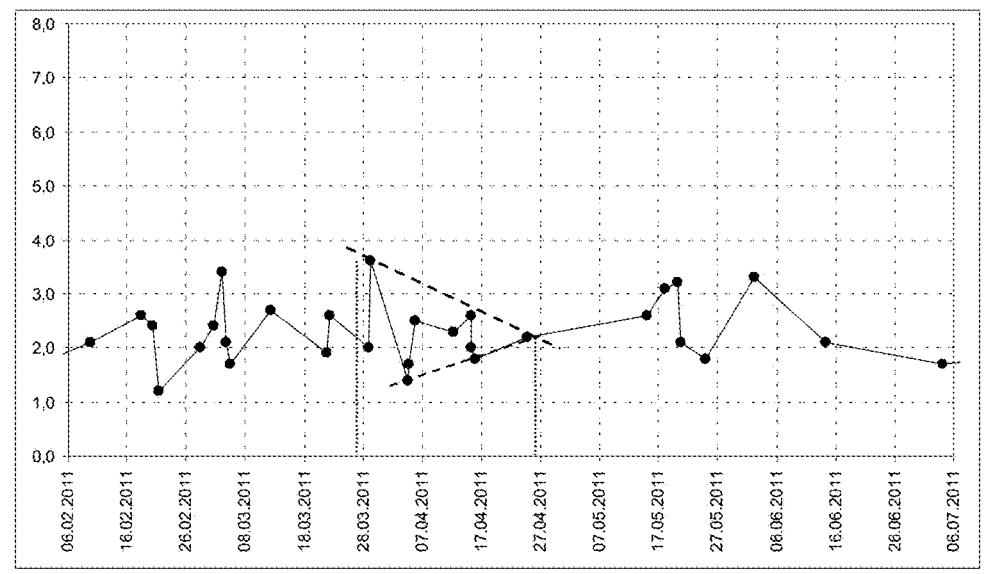
FIG. 46. An exemplary indicator sequence ("attenuation wedge"), identified according to the present invention.

FIG. 46 presents a typical sequence, provided in a time series. FIG. 46 shows the magnitude of seismic event sequences converged into one geographic point of observation. Such a sequence is defined as converging oscillations having a marked attenuation focus. This attenuation focus determines the moment of a forecastable relief of a seismic tension, which presents itself as a significant earthquake.

In order to expose such phenomena, the present invention suggests developing a set of methods or algorithms combined in a single analytical software package for identifying seismic events indicators.

The first step of the algorithmic search process comprises identifying the constant component of the basic series, X(t). This identification is performed by a transition to the series of first differences, X1(t), which is symmetrical in respect of the average value, X1=0.

The "attenuation wedge" to be determined in the first differences series is a sequence of the series, X1, components, which can be modeled in a first approximation as an attenuation oscillations equation:

$$X1(t) = A \cos \omega t \cdot \exp(-\lambda t) \quad (1)$$

The characteristics of the attenuation wedge will be analyzed separately for positive and negative components of the series, X1(t).

Next, it is necessary to choose a certain slot (i.e. range) in the time series, X1, of length, N, identify local maximums for the positive subsequence (+X1) within the slot, and calculate the factors for the regression equation maximum, X11=A11−B11t, and the determination factor, $R^2$.

The same is done for the negative subsequence (−X1) and the factors/coefficients of the equation, X12=A12+B12t, are calculated. If the coefficient B11 is significantly less than zero, and the coefficient B12 for the negative subsequence (−X1) is significantly greater than zero, then there is a wedge within the window.

Figure 47:
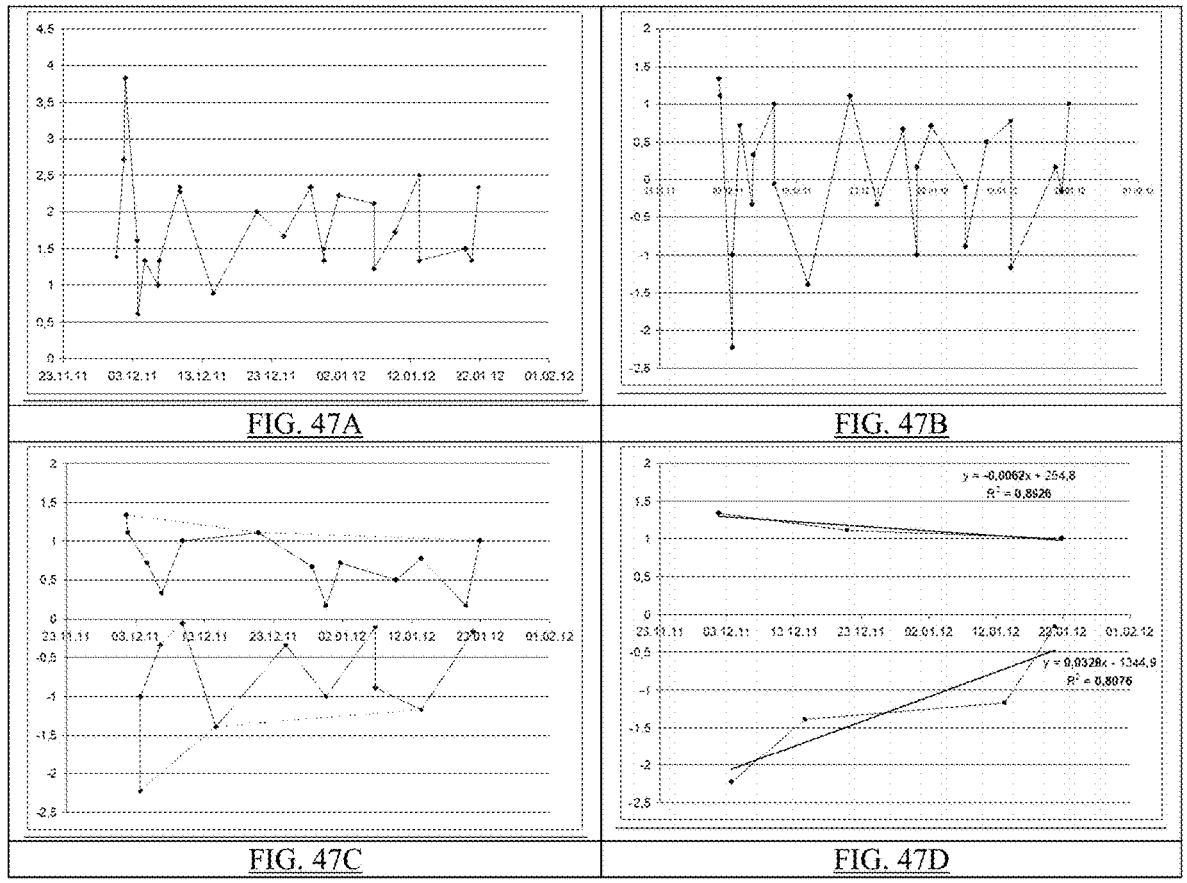
FIGS. 47A-47D. The stage sequence of analyzing seismic data time series and calculating parameters of regression equations.
Figure 48:
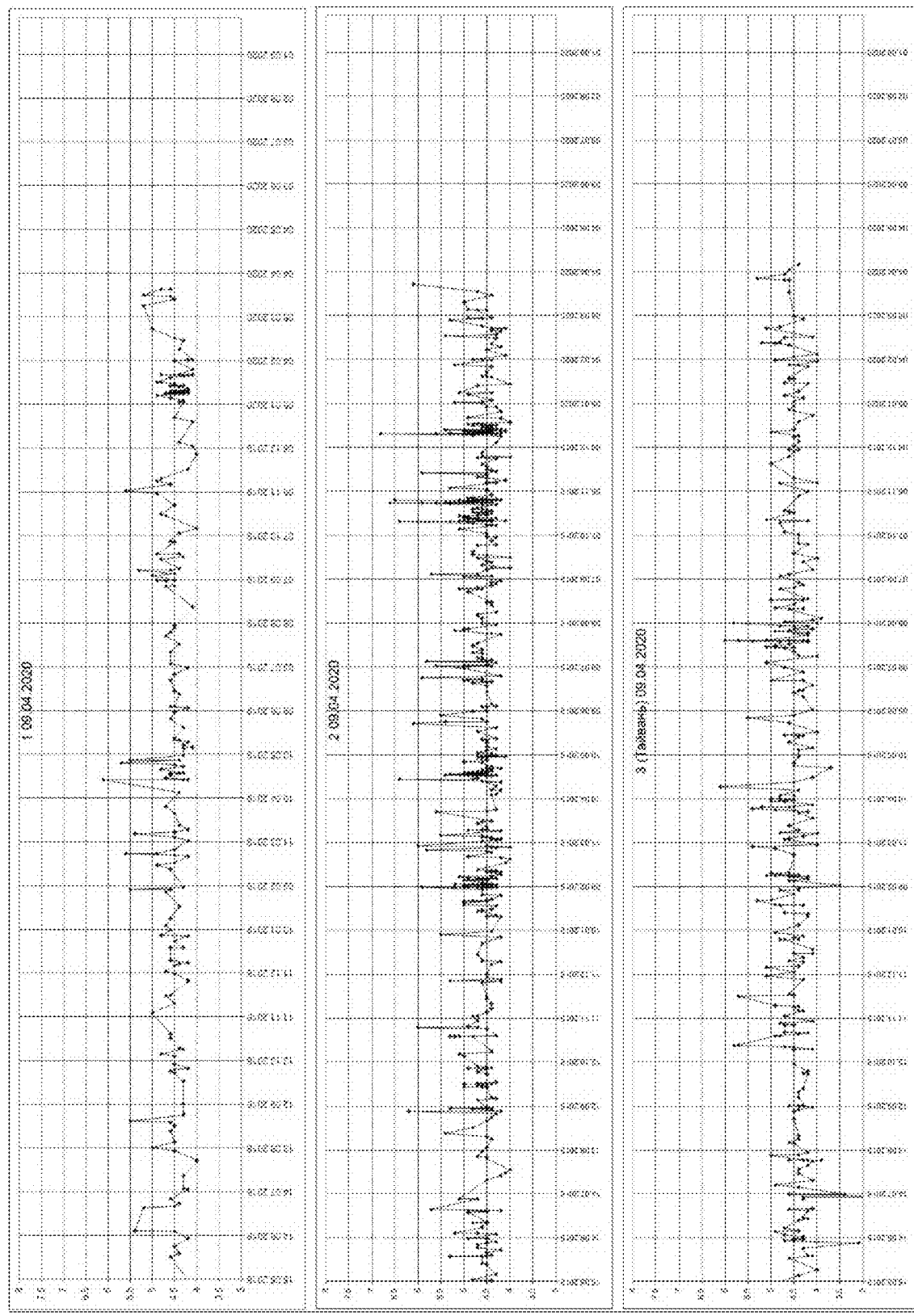
FIG. 48. Cell data catalog (Fragment of the forecast of the Philippine earthquake on Apr. 10, 2020).
Figure 49:
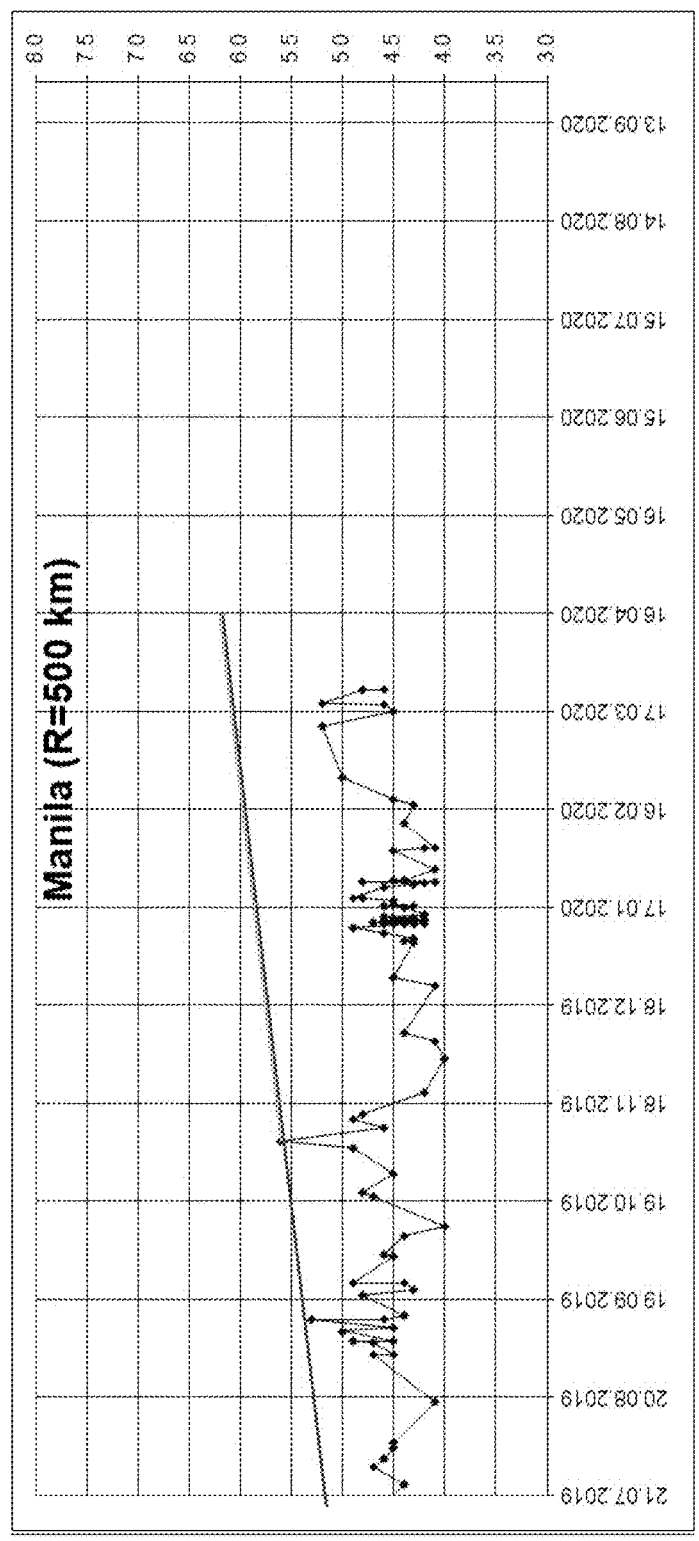
FIG. 49. Cell data catalog with upper energy levels (Fragment of the forecast of the Philippine earthquake on Apr. 10, 2020).
Figure 50:
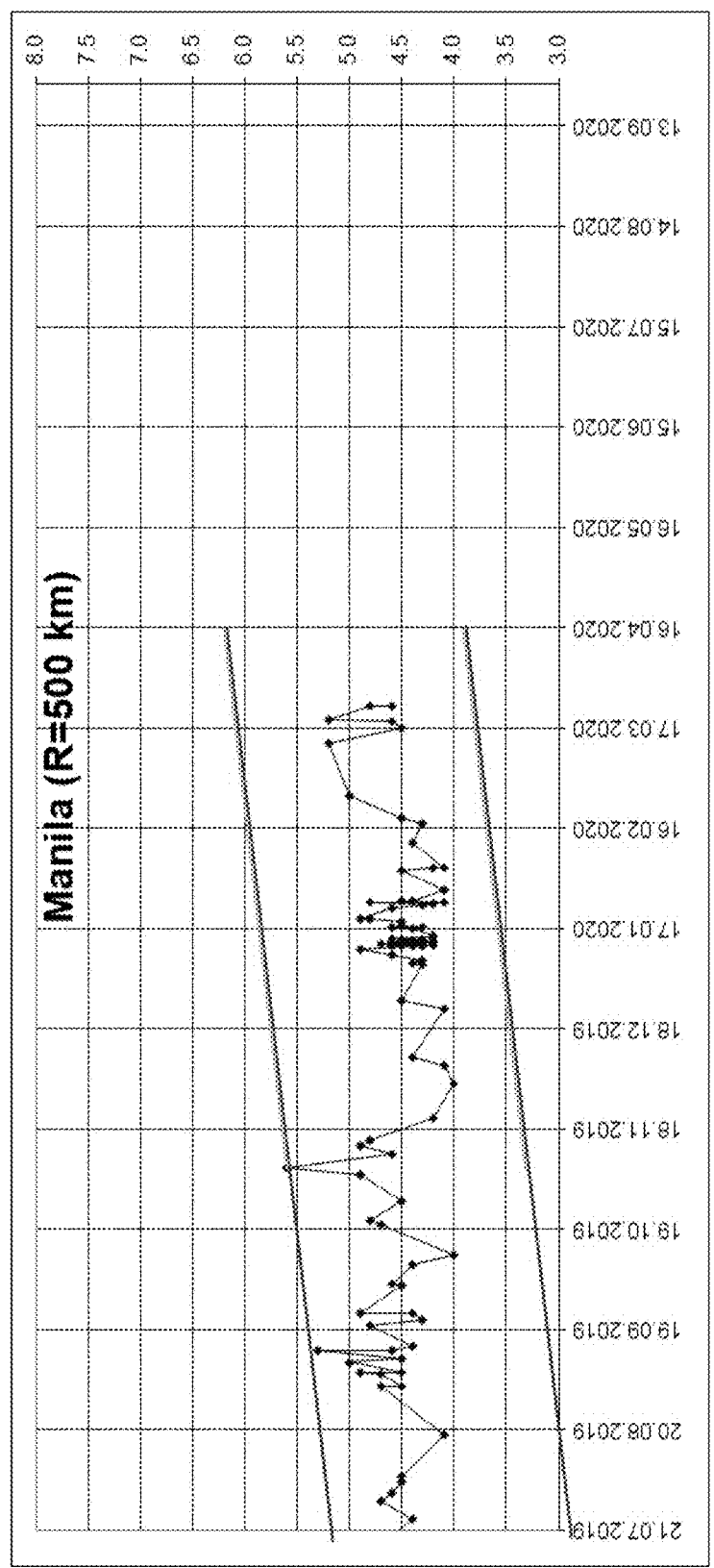
FIG. 50. Cell data catalog with upper and lower energy levels (Fragment of the forecast of the Philippine earthquake on Apr. 10, 2020).
Figure 51:
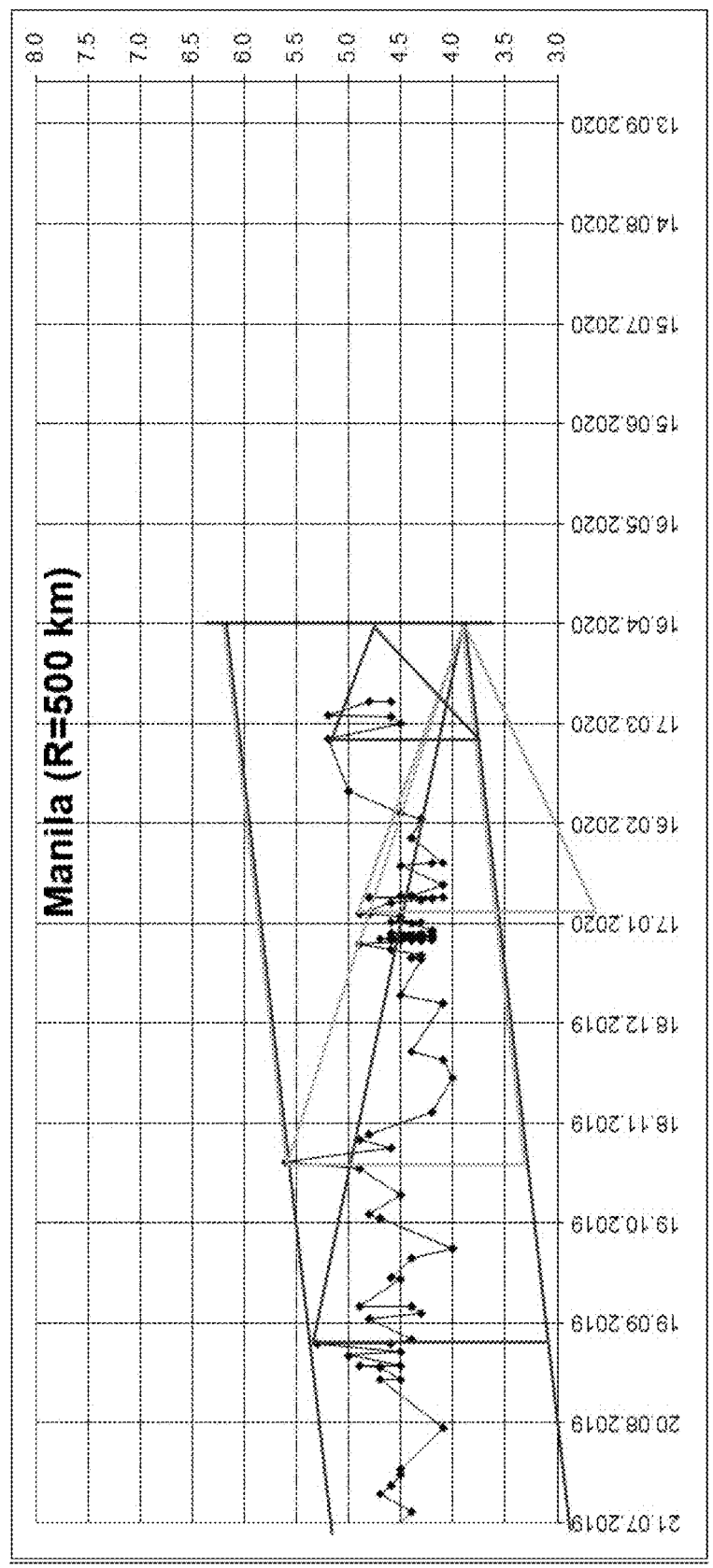
FIG. 51. Cell data catalog with energy levels and wedges (Fragment of the forecast of the Philippine earthquake on Apr. 10, 2020).
Figure 52:
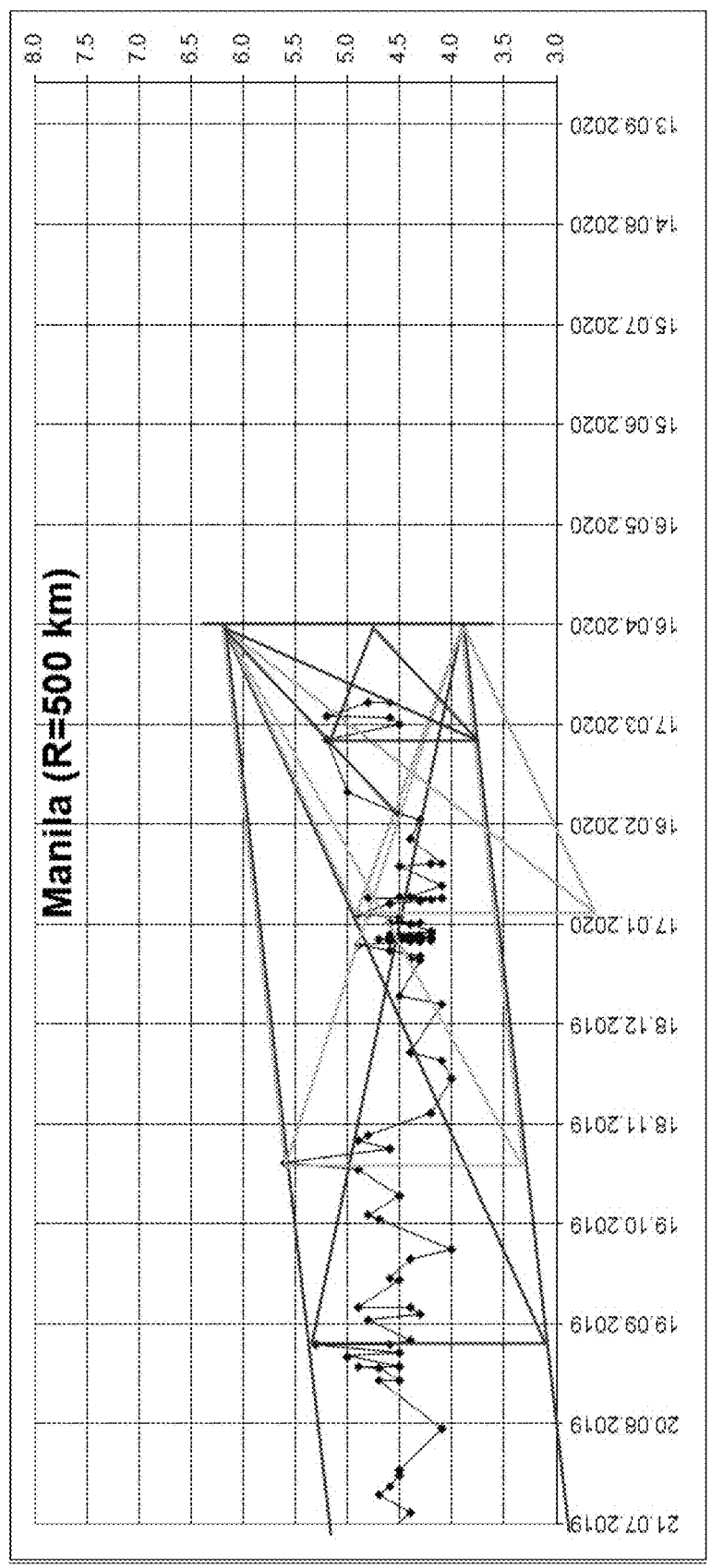
FIG. 52. Cell data catalog with energy levels, wedges, and time arrows (Fragment of the forecast of the Philippine earthquake on Apr. 10, 2020).
Figure 53:
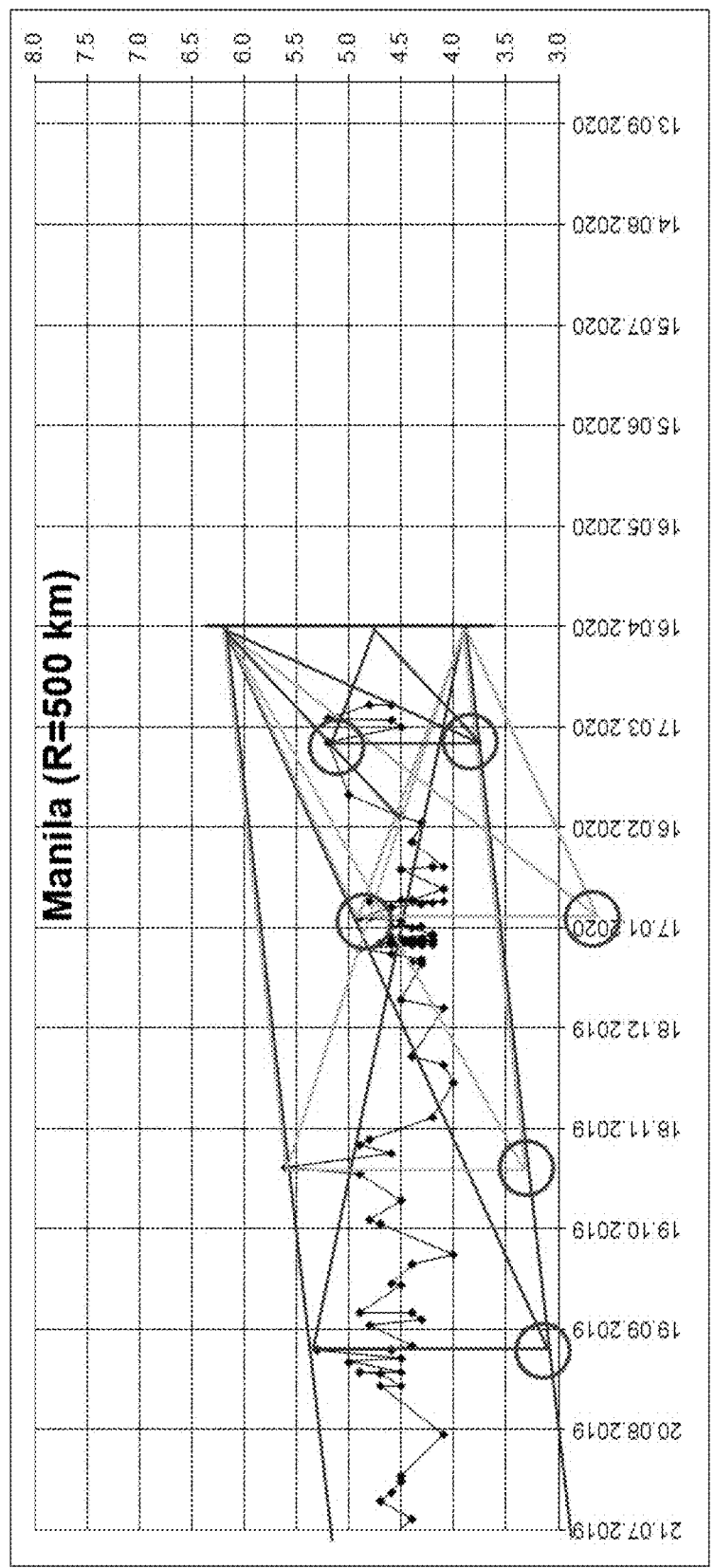
FIG. 53. Analysis of energy centers (Fragment of the forecast of the Philippine earthquake on Apr. 10, 2020).
Figure 54:
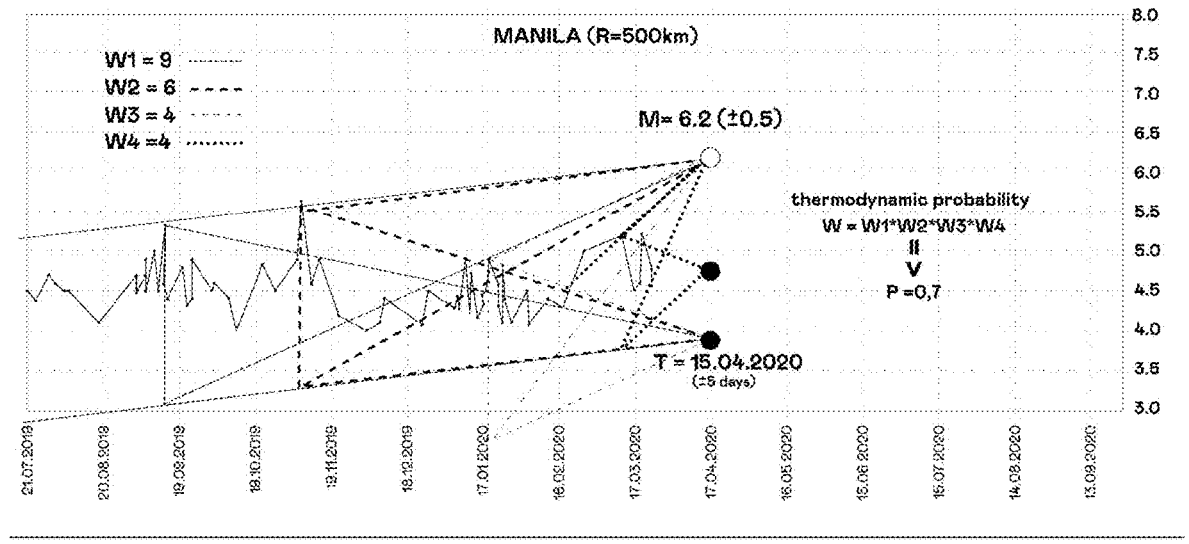
FIG. 54. An exemplary overall forecast development, based on the present invention (Fragment of the forecast of the Philippine earthquake on Apr. 10, 2020).

The sequence of calculations illustrated in stages is shown in FIGS. 47A-47D. FIG. 47A show the basic time series. FIG. 47B shows the series of first differences. FIG. 47C shows the positive and negative component series of first differences, the dotted one-series of local maximums (minimums), FIG. 47D shows the calculation of regression equation parameters.

Thereafter, the point of intersection between the upper and lower regression curves is calculated via the following relationship:

$$t_0 = \frac{A11 - A12}{B11 + B12} \quad (2)$$

If the sequence in the slot has the shape of a wedge, a linear trend is identified based on positive and negative subsequences, and the oscillation frequencies within the slot are calculated for the series cleared of the trend, using the method of extreme points. If a wedge has been determined correctly, the frequencies must be close in their values.

Finally, the slot can be shifted one term of the series to the right without changing its length, and calculations may be performed again.

Using the accumulated data about the seismic activity and the algorithm in question, one can analytically determine the optimum wedge identification parameters for the given area. Namely, one can determine the threshold value parameters of the approximation, A1 and A2, line inclination, the determination factors, $R_1^2$ and $R_2^2$, and the optimal slot size. Using these parameters, one must promptly calculate the possibility of a wedge formation based on the current monitoring dates, and predict seismic events.

The end software product is a program which takes in structured data about seismic events and returns a predictable date based on generated graphs. In a training mode, a set of parameters is determined allowing to identify an attenuation wedge as detailed above. Based on the parameters identified, an analysis of current seismic data is created, attenuation wedges are identified and their parameters are determined.

In FIGS. 48-54, predictive patterns for a preliminary forecast for Manila (Philippines), is shown. The more predictive patterns, the more likely an earthquake. On April 15, ±5 days, within a 500 km radius of Manila, there is shown to be a likelihood (0.6-0.7) of an earthquake with a magnitude of 6.0-6.5.

Example 1

1. Collection and Preparation of Information.

1.1. Data Search

To accomplish the task, open source data from the US Geological Survey (https://earthquake.usgs.gov/) was used. Using the US Geological Survey website, the following exemplary data was retrieved from the database: Table 3:

TABLE 3

| DATE | LAT | LON | H | M |
|---|---|---|---|---|
| 19 Jan. 2020 12:59 | 14.0157 | 120.8913 | 10 | 4.5 |
| 20 Jan. 2020 4:31 | 15.5968 | 119.3558 | 10 | 4.8 |
| 20 Jan. 2020 5:33 | 15.7158 | 119.2376 | 10 | 4.9 |
| 23 Jan. 2020 13:05 | 12.5693 | 123.5292 | 35.19 | 4.6 |
| 24 Jan. 2020 13:06 | 18.1189 | 121.1114 | 35 | 4.3 |
| 24 Jan. 2020 21:09 | 18.1927 | 121.1694 | 41.65 | 4.2 |
| 25 Jan. 2020 4:56 | 15.7038 | 119.2125 | 10 | 4.8 |
| 25 Jan. 2020 7:47 | 15.6987 | 119.2215 | 10 | 4.1 |
| 25 Jan. 2020 11:06 | 15.7804 | 119.235 | 10 | 4.5 |
| 25 Jan. 2020 12:56 | 15.7243 | 119.2992 | 10 | 4.4 |
| 29 Jan. 2020 3:51 | 15.8542 | 119.5021 | 10 | 4.1 |
| 3 Feb. 2020 21:44 | 15.7307 | 119.2637 | 10 | 4.5 |
| 4 Feb. 2020 10:27 | 15.5852 | 119.2924 | 10 | 4.2 |
| 4 Feb. 2020 13:56 | 14.4766 | 121.0321 | 144.37 | 4.1 |
| 12 Feb. 2020 0:45 | 14.0514 | 120.2228 | 81.71 | 4.4 |
| 17 Feb. 2020 21:02 | 13.4555 | 120.6301 | 49.41 | 4.3 |
| 19 Feb. 2020 9:36 | 17.5983 | 119.875 | 10 | 4.5 |
| 26 Feb. 2020 0:23 | 15.8708 | 119.2231 | 10 | 5 |
| 12 Mar. 2020 22:00 | 14.6765 | 119.122 | 10 | 5.2 |
| 17 Mar. 2020 5:06 | 13.5995 | 120.9335 | 142.94 | 4.5 |

TABLE 3-continued

| DATE | LAT | LON | H | M |
|---|---|---|---|---|
| 19 Mar. 2020 6:49 | 14.9634 | 120.155 | 66.53 | 4.6 |
| 19 Mar. 2020 20:08 | 14.4841 | 124.0742 | 10.35 | 5.2 |
| 23 Mar. 2020 20:23 | 15.8153 | 119.0233 | 10 | 4.8 |
| 23 Mar. 2020 20:56 | 15.8273 | 119.3013 | 7.09 | 4.6 |

1.2. Assessment of the geo-environment stress-strain states in the forecast area. To assess the stress-strain state, earthquakes from the database were analyzed, assessing their magnitude potential and location.

Earthquakes are scattered fairly evenly across the Philippines, the magnitude span is rather big with a potential for earthquakes of magnitudes over 6.0. It is necessary to scan the area in question by means of information cells of different sizes to locate the epicenter of the coming strong earthquake.

1.3. Scanning the prognostic area (in earthquake catalogs) by means of information cells corresponding to various magnitudes of predicted intense events. Based on many years of experience in geodynamic monitoring and forecasting strong earthquakes, a correlation is calculated between the analyzed amount of data and the predicted magnitude. In this example, it was determined necessary to scan the area under surveillance by means of information cells from D500 to D1000. As a result, a set of data catalogs for each information cell is obtained.

2. Forecasting Earthquakes

Analyze each cell to detect prognostic signs of preparation for a strong earthquake. This report contains a comprehensive analysis of only one cell, for which a forecast of an earthquake (M=6.2) between 10 and 20th of April, 2020 was produced.

2.1. Representation of seismic processes in "magnitude—time" coordinates for each information cell. A representation of data in "magnitude-time" coordinates was created to show the catalog representativity. See FIG. 48.

2.2. Identifying energy levels. Here one can see how maximum and minimum energy levels are identified. See FIG. 49.

2.3. Restoration of low-energy processes (events). Restoration of a bottom energy level based on an upper energy level. See FIG. 50.

2.4. Singling out key components in the structure of geodynamic processes, calculation of slope angles for maximum and minimum energy levels; assessment of seismic process intensity ("power level"). Next, single out and build prognostic structures in the energy process to establish the time of a forecast earthquake. See FIG. 51.

2.5. Building time arrows in a "magnitude—time" system of coordinates. Identifying time arrows to assess magnitude of a forecast earthquake. See FIG. 52.

2.6. Identification of real and virtual energy centers controlling the seismic process, which are formed in energy level break points. Verifying the reliability of a strong earthquake forecast requires analyzing existence and stability of energy centers. See FIG. 53.

Validation of Earthquake Activity and Comparison with the Present Invention

On Apr. 10, 2020 at 16-44 (UTC) to the north of Manila, an earthquake with a magnitude of 5.9 (or 6.3, according to other data) took place. This was forecast by the present invention in terms of both time and magnitude. The epicenter was located with a radius of 500 km, with an error of 30% (500+/−150 km). This confirmed the accuracy claimed in the forecast, which can be enhanced further. It is known that a strong earthquake is normally followed by an aftershock seismic process in the focal point area, which was confirmed by an earthquake of magnitude, M=5.0, on 15.04.2020, being a rather strong aftershock of the earthquake of magnitude, M=5.9, on 10.04.2020.

Figure 56:
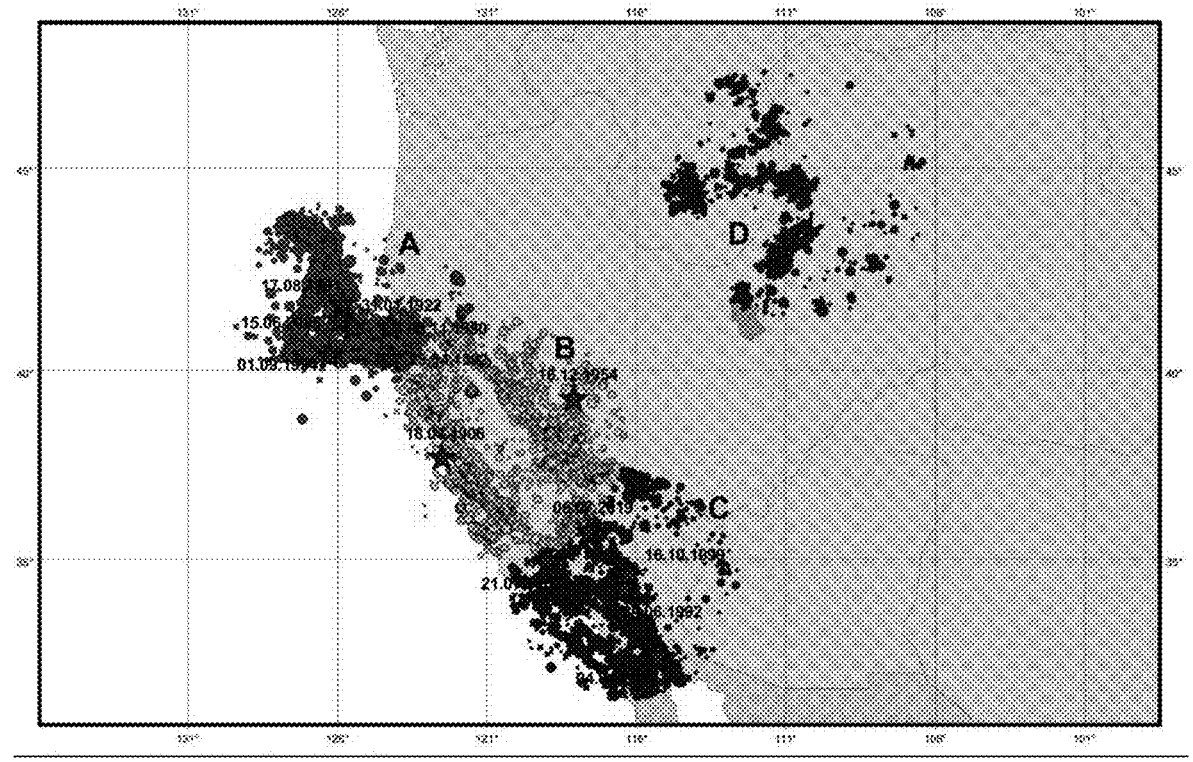
FIG. 56. Highlighted areas in California and surroundings for forecasting according to the present invention.

The present invention's forecast of earthquakes in California for the near future: (1) Zone B (350 km=217 mi, around San Francisco, see FIG. 56); Magnitude: 4.8-5.0; Time interval: May 16-19. (2) Zone A (see FIG. 56), North of San Francisco; Magnitude: 5.0-5.5; Time interval: May 22-29. This forecast was created on May 14, 2020.

Algorithm for Building Parallelograms of the Present Invention, Generalized

The following generalized algorithm may also be used to carry out the present invention:

Build in the coordinates of magnitude-time (see, e.g., FIG. 57) all known historical earthquakes for the selected area (in the form of points in a Cartesian coordinate system). Choose a plot of land no more than 1000 km in radius.

Programmatically build all the possible lines that can be drawn through the points (in time, there is preferably practically enough data for the last three years). The thermodynamic probability in the basic version is calculated by the number of points corresponding to earthquake events. When drawing a line, it is possible to accurately locate a point on the line with 99.8 percent accuracy. The small error is due to the fact that existing earthquakes are recorded with slightly varying magnitudes in different countries; therefore, tolerance levels depend on the accuracy of the source data.

The points RD, RT are calculated; they do not exist from the known information. All other points correspond to real statistics from prior earthquakes. Point RT is the forecast of the future earthquake. Point RD is a forecast point by date, which is calculated based on the calculation of the energy wedge. The LT-LD and RT-RD lines are parallel to the axis of magnitude, with tolerance-deviation. The tolerance-deviation is preferably not more than 5%, ideally 0, and depends on the accuracy of the source data. It is important to first calculate the RD point, then, the triangle LT-RD-LD—which corresponds to attenuation wedge, as described in more detail above.

Figure 57:
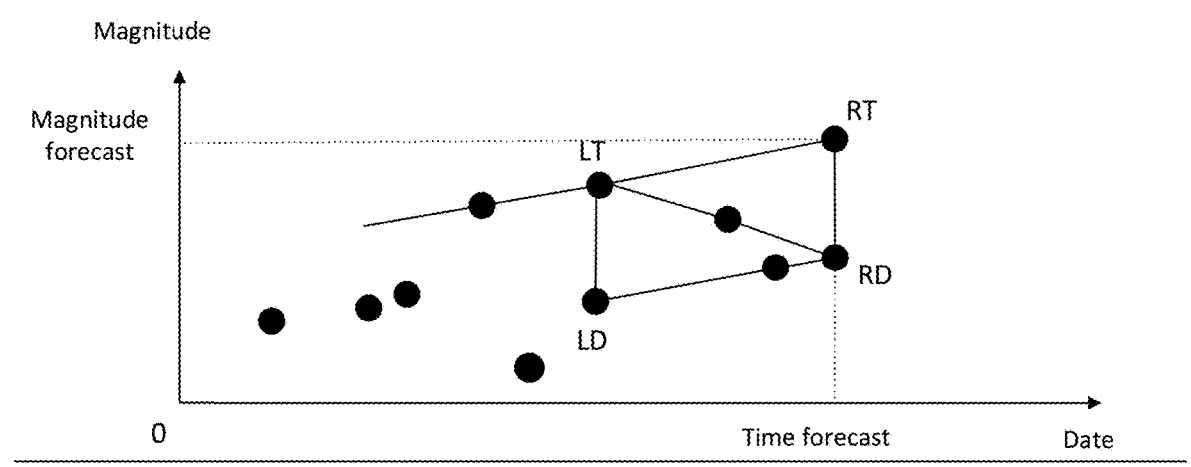
FIG. 57. An exemplary use of an energy parallelogram according to the present invention.

The parallel sides of the parallelogram are pairwise equal to each other. The upper line is considered to be the bottom (this is how the forecast turns out). There are at least 2 points on the LD-RD and LT-RD lines (before calculating the RD point). To the left of the LT point, at least one point lies on the common line. To the right of the LT point, most often initially there is not a single event point. The physical meaning of FIG. 57 is the accumulation and discharge of energy in a seismic source. The energy of smaller cracks accumulates, followed usually by a calm period and then a discharge by a large earthquake. In some cases, after a calm period, there is a smaller earthquake, which accurately dictates the epicenter of a larger upcoming earthquake.

Find all pairs of parallel lines. Build a fading energy wedge, as described above.

The starting point of the top line is the top left point of the parallelogram. It is noted that there can also be many event points to the left of this point (and there should not be a single point to the right). The length of the upper line of the energy parallelogram must be calculated from this point.

Form all possible potential energy parallelograms. To do this, calculate the length of the bottom line of the parallelogram and extend the top line (since in the parallelogram, the opposite sides should be equal).

The right upper point of the parallelogram will indicate the nearest predictable earthquake. The coordinate system will show the time and magnitude of the nearest predictable earthquake. The forecasted earthquake depth can be calculated as the arithmetic average of the earthquake depths corresponding to the points on which the parallelogram was built. To determine the forecast of the location of the epicenter of the nearest predictable earthquake, one may also use a circle with the center of the latest small magnitude earthquakes (less than M=3). Detected anomalies of heat (i.e., infrared, registered via satellite) or radon (registered via gas analyzers) will indicate the location of the earthquake epicenter most accurately.

The normalized multiplication of all thermodynamic probabilities will provide for a confidence (i.e. probability) related to the forecast.

The more parallelograms that converge at one forecast point, the more reliable the forecast. Also, the more points lying on the lines of the parallelogram, the more reliable the forecast.

Sharp amplitude anomalies of the electromagnetic background of the earth, the radon content in the air, and heat (which is visible in the infrared range) are the final harbingers of a future earthquake, the detection of which allows for the methods of the present invention to determine in more detail the location of a future epicenter. See FIGS. 25-31, which show the electromagnetic harbingers of a future earthquake (i.e., changes in the diurnal variations of the natural electromagnetic field of the Earth). At the final stage (e.g., one week before the earthquake), such changes may be used to finalize the earthquake forecast. These changes, together with infrared anomalies and an increase in the concentration of radon in the air, complete the prediction process and indicate imminent seismic activity.

Within the scope of the invention is firmware, hardware, software and computer readable-media including software which is used for carrying out and/or guiding the methodologies described herein, particularly with respect to radioactive (and nuclear) threat detection. Hardware optionally includes a computer, the computer optionally comprising a processor, memory, storage space and software loaded thereon. The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprise(s)", "include(s)", "have" and their conjugates mean "including but not limited to". The scope of the invention is limited only by the following claims.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for predicting seismic activity, comprising:
providing one or more data catalogs for an area,
constructing magnitude-time coordinates for one or more information cells within said area, said magnitude-time coordinates forming a seismic process structure,
identifying energy levels of the seismic process structure,
identifying elements within the seismic process structure, the identified elements comprising:
obliquity angles of maximum energy levels,
obliquity angles of minimum energy levels, and
a potential of the seismic process structure, the potential comprising an average increment between minimum and maximum energy levels of the seismic process structure,
constructing one or more time arrows and calculating one or more measuring angles of the one or more time arrows, the one or more measuring angles of the one or more time arrows being relative to a time axis of the seismic process structure,
identifying instant energy centers, the instant energy centers comprising variations in energy levels,
analyzing a variability of:
the elements within the seismic process structure,
the one or more time arrows and the one or more measuring angles, and
the instant energy centers, and
predicting a seismic event based on said analyzing.

2. The method of claim 1, wherein the instant energy centers are indicated by an attenuation wedge, the attenuation wedge being locatable along a graphical seismic process representation.

3. The method of claim 2, wherein the attenuation wedge is modeled using an attenuation oscillations equation, the attenuation oscillations equation being $X1(t)=A\cos\omega t \cdot \exp(-\lambda t)$, wherein $X1(t)$ represents a series of values of the attenuation wedge over time, A represents a magnitude of a signal recorded by a reference instrument, $\omega$ represents a nonlinear pendulum's frequency, t represents time, and $\lambda$ represents a parameter of nonlinearity".

4. The method of claim 3, wherein characteristics of the attenuation wedge are analyzed separately for positive components and negative components of the series, $X1(t)$.

5. The method of claim 4, further comprising calculating one or more points of intersection between upper and lower regression curves formed as results of the separate analyzing of the positive components and the negative components of the series, $X1(t)$.

6. The method of claim 1, further comprising detecting heat anomalies prior to the seismic event.

7. The method of claim 1, further comprising one or more energy parallelograms.

8. The method of claim 1, further comprising detecting radon anomalies prior to the seismic event.

9. The method of claim 1, further comprising:
constructing an energy curve, $A^2(\omega)$, the curve having the following parameters: $\omega_0$, $\alpha$, $\lambda$, and F, wherein $\omega_0$ represents a nonlinear pendulum's frequency, $\alpha$ represents an attenuation parameter, $\lambda$ represents a parameter of nonlinearity, and F represents coercive forces,
identifying a point in time when a system depicted by the energy curve resembles a wedge,
computing a change in the energy curve based on an amplitude of a counter-entropy event, and
approximating a number of iterations until a significant seismic event is determined to occur, the number of iterations being translatable into a time value, wherein the time value is used to predict an onset of the seismic activity.

10. The method of claim 1, further comprising detecting an ultra-small event.

11. The method of claim 1, further comprising analyzing a focal point's energy structure.

12. The method of claim 1, further comprising detecting atmospheric pressure changes.

13. The method of claim 1, wherein a forecast is provided 1-3 months in advance of the seismic event.

14. The method of claim 1, wherein a forecast is provided 1-10 days in advance of the seismic event.

15. The method of claim 1, further comprising receiving data from local seismometers.

16. The method of claim 1, further comprising performing a geodynamic monitoring with inertial seismometers.

* * * * *